(12) United States Patent
Kotidis et al.

(10) Patent No.: US 8,780,347 B2
(45) Date of Patent: Jul. 15, 2014

(54) QCL SPECTROSCOPY SYSTEM AND APPLICATIONS THEREFOR

(75) Inventors: Petros Kotidis, Framingham, MA (US);
Erik Deutsch, Brookline, MA (US);
Ninghui Zhu, Winchester, MA (US);
Dan Cavicchio, Dorset, VT (US)

(73) Assignee: Block Engineering, LLC, Marlborough, MA (US)

( * ) Notice: Subject to any disclaimer, the term of this patent is extended or adjusted under 35 U.S.C. 154(b) by 67 days.

(21) Appl. No.: 13/159,225

(22) Filed: Jun. 13, 2011

(65) Prior Publication Data

US 2012/0033220 A1    Feb. 9, 2012

Related U.S. Application Data

(60) Provisional application No. 61/354,136, filed on Jun. 11, 2010, provisional application No. 61/410,231, filed on Nov. 4, 2010, provisional application No. 61/475,053, filed on Apr. 13, 2011.

(51) Int. Cl.
*G01J 4/00* (2006.01)

(52) U.S. Cl.
USPC .......................................... 356/364; 356/370

(58) Field of Classification Search
USPC ......... 356/364–370, 445–448, 451, 454, 455, 356/459, 460, 468, 469, 480; 250/339.06; 372/92–98, 43.01
See application file for complete search history.

(56) References Cited

U.S. PATENT DOCUMENTS

| | | |
|---|---|---|
| 5,877,862 A | 3/1999 | Nelson et al. |
| 6,627,412 B1 | 9/2003 | Manning et al. |
| 6,737,651 B1 | 5/2004 | Lendl |
| 7,115,869 B2 | 10/2006 | Shelley et al. |
| 7,697,976 B2 | 4/2010 | Wu et al. |
| 2009/0180122 A1* | 7/2009 | Federici ................. 356/451 |
| 2009/0225802 A1 | 9/2009 | Day et al. |
| 2010/0045977 A1 | 2/2010 | Puzey |
| 2010/0140476 A1 | 6/2010 | Werner et al. |
| 2011/0080311 A1* | 4/2011 | Pushkarsky et al. ......... 342/14 |

FOREIGN PATENT DOCUMENTS

| | | |
|---|---|---|
| DE | 10 2007 062 651 A1 | 6/2009 |
| WO | 2010062752 A1 | 6/2010 |

OTHER PUBLICATIONS

"610/620-IR, FT-IR Microscopy and Imaging Solutions," Varian, Inc., 2008-2009, pp. 2, 5, and 7.
Capasso, F., "Quantum cascade lasers penetrate the market," Interview by Marie Freebody, Optics & Laser Europe, Feb. 2009, p. 13.
Hinkov, B. et al., "Broad band tunable quantum cascade lasers for stand-off detection of explosives," Proceedings of the SPIE, vol. 7484, Sep. 1, 2009, pp. 748406. Abstract only.

(Continued)

*Primary Examiner* — Tri T Ton
(74) *Attorney, Agent, or Firm* — Houston & Associates, LLP

(57) ABSTRACT

A spectroscopy system comprising at least two laser modules, each of the laser modules including a laser cavity, a quantum cascade gain chip for amplifying light within the laser cavity, and a tuning element for controlling a wavelength of light generated by the modules. Combining optics are used to combine the light generated by the at least two laser modules into a single beam and a sample detector detects the single beam returning from a sample.

21 Claims, 39 Drawing Sheets

(56) References Cited

OTHER PUBLICATIONS

Lambrecht, A. et al., "Continuous glucose monitoring by means of fiber-based, mid-infrared laser spectroscopy," Applied Spectroscopy, vol. 60, No. 7, 2006, pp. 729-736. Abstract only.

Mehta, N.K. et al., "Development of an In Situ Spectroscopic Method for Cleaning Validation Using Mid-IR Fiber Optics," Fiber Optics, Spectroscopy, vol. 18, No. 4, Apr. 2003, pp. 14-16 and 18-19.

Nicholson, S. "MIR Spectroscopic Sensing: Identify, Measure, Protect," International Quantum Cascade Lasers School & Workshop, Sep. 19, 2008, Cascade Technologies, 26 pages.

So, S.G. et al., "Development of Digital Signal Processor Controlled Quantum Cascade Laser Based Trace Gas Sensor Technology," IEEE Sensors Journal, vol. 6, No. 5, Oct. 2006, pp. 1057-1067.

Wang, P. et al., "Infrared Spectroscopy using Quantum Cascade Lasers," Bruker Optics, School of Engineering and Applied Sciences, Harvard University, Jun. 2009, 19 pages.

Weida, M.J. et al., "Quantum cascade laser based replacement for FTIR microscopy," Daylight Solutions, Proceedings of the SPIE, vol. 7902, 2011, 7 pages.

Wysocki, G. et al., "Widely tunable mode-hop free external cavity quantum cascade laser for high resolution spectroscopic applications," Applied Physics B, Lasers and Optics, Springer-Verlag, vol. 81, 2005, pp. 769-777.

International Search Report mailed Feb. 7, 2012, from counterpart International Application No. PCT/US2011/040217, filed on Jun. 13, 2011.

International Preliminary Report on Patentability mailed Dec. 27, 2012, from counterpart International Application No. PCT/US2011/040217, filed on Jun. 13, 2011.

* cited by examiner

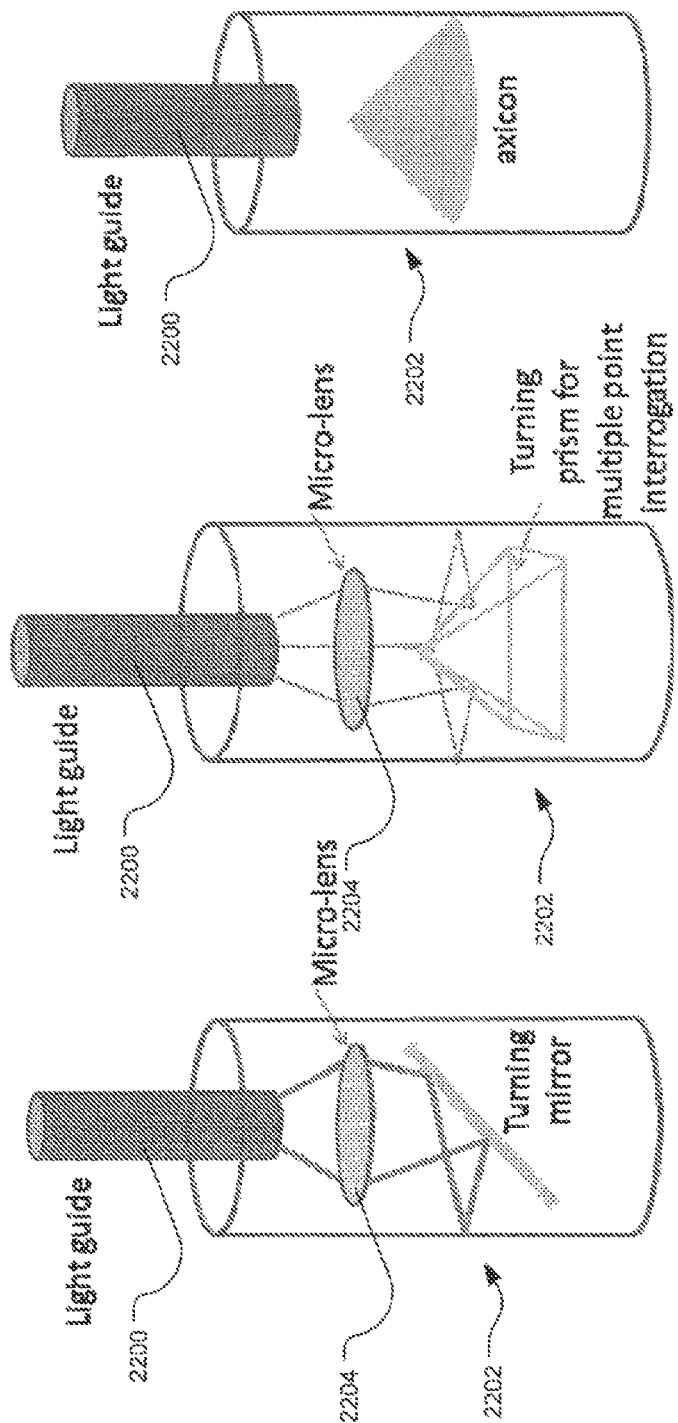

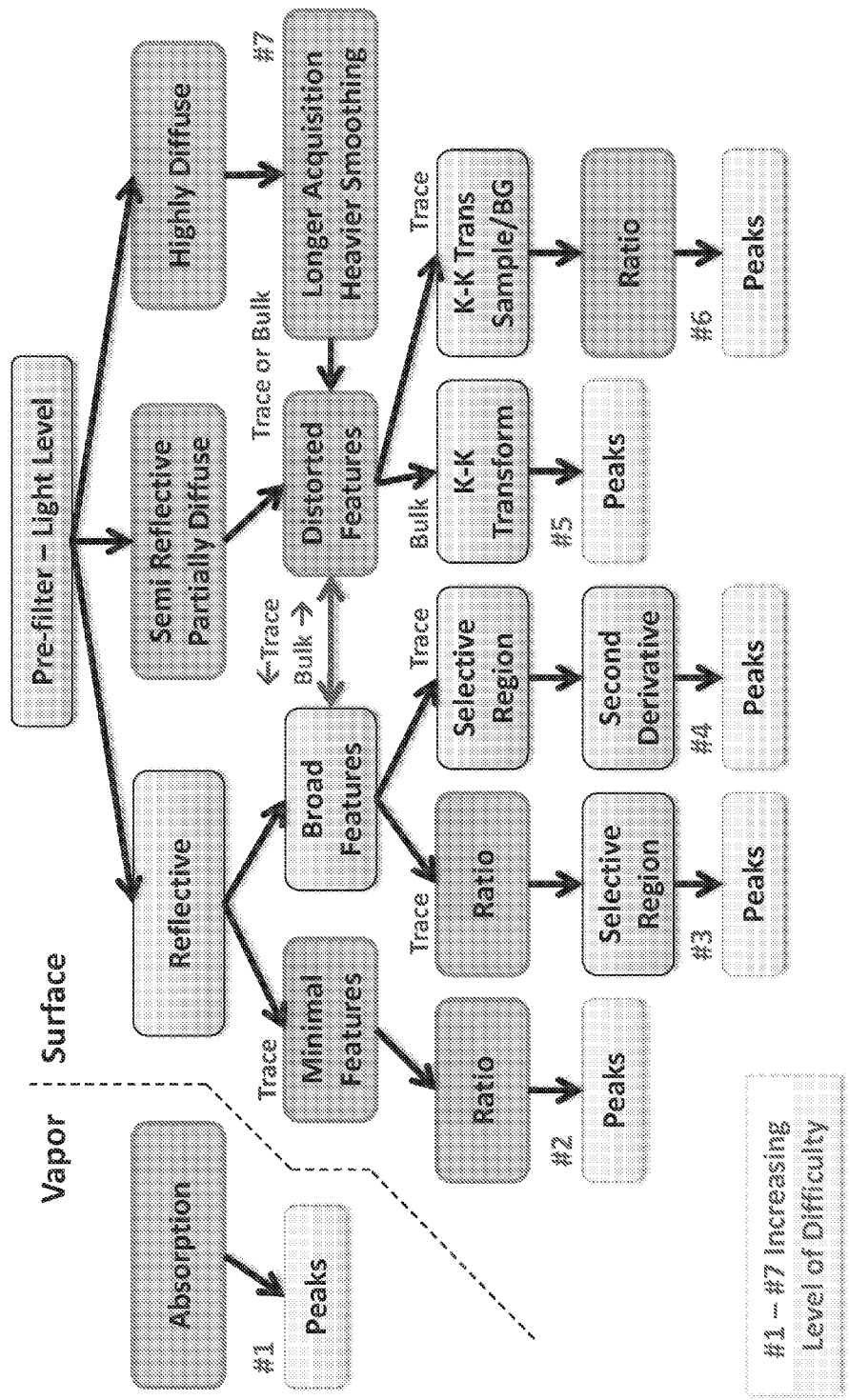

QCL SPECTROSCOPY SYSTEM AND APPLICATIONS THEREFOR

RELATED APPLICATIONS

This application claims the benefit under 35 USC 119(e) of U.S. Provisional Application Nos. 61/354,136, filed on Jun. 11, 2010, 61/410,231, filed on Nov. 4, 2010 and 61/475,053, filed on Apr. 13, 2011, all of which are incorporated herein by reference in their entirety.

BACKGROUND OF THE INVENTION

Grating tuned external cavity semiconductor lasers have been used for spectroscopy sources for many decades. Recently, wide band infrared gain chips have been available based on quantum cascade technology. Quantum cascade lasers (QCL) generate light in the mid to far infrared (IR) using intersubband transitions in a repeated stack of semiconductor multiple quantum well heterostructures.

SUMMARY OF THE INVENTION

In general, according to one aspect, the invention features a spectroscopy system comprising at least two laser modules, each of the laser modules including a laser cavity, a quantum cascade gain chip for amplifying light within the laser cavity, and a tuning element for controlling a wavelength of light generated by the modules, combining optics for combining the light generated by the at least two laser modules into a single beam, and a sample detector for detecting the single beam returning from a sample.

In embodiments, three of the laser modules are used and the tuning element comprises a grating or a Fabry-Perot tunable filter.

Some applications require projection optics for projecting the single beam to a sample. A sighting laser and a housing with attached handle are also provided, wherein the laser modules are contained within the housing.

In some embodiments, retroreflectors positioned in a room, wherein the single beam is projected to the retroreflectors and then returned to the sample detector.

In other examples, a gas cell is provided within a portable hand-held housing, wherein the laser modules and the vapor cell are contained within the housing, the single beam analyzing air in the gas cell.

One application uses a system for puffing air onto shoes and a system for collecting the air, the single beam analyzing the collected air. A magnetometer can also be provided.

In general, according to another aspect, the invention features a quantum cascade laser microscopy system comprising the spectroscopy system, wherein the sample detector comprises a detector array, a light microscope for projecting the single beam onto the sample, and an X-Y scanning stage for scanning the sample under the microscope.

In general, according to another aspect, the invention features a method for detecting recently disturbed earth comprising scanning soil with a quantum cascade laser spectroscopy system from a stand-off distance, recording the absorption spectra of the scanned soil, establishing a baseline spectra of soil that has not been recently disturbed, and detecting changes in the spectra consistent with recent disturbance of the soil.

Embodiments further comprise scanning the soil with ground penetrating radar.

The system can be deployed in a hand-held arrangement by an operator on-foot, on an interrogation arm, or on unmanned aerial vehicles.

In general, according to another aspect, the invention features a method for testing a surface for contaminants in a pharmaceutical environment comprising directing emission from a quantum cascade laser spectroscopy system towards a pharmaceutical surface at a stand-off distance, detecting an absorption spectra of the pharmaceutical surface using the quantum cascade laser spectroscopy system, comparing the absorption spectra with a standard, and calculating a level of contaminants present on the pharmaceutical surface.

In embodiments, the pharmaceutical surface is the interior of a reaction vessel. The method involves comparing the level of contaminants to a pre-determined acceptable level and, if the level of each contaminant is not below the acceptable level, cleaning the pharmaceutical surface and retesting the level of contaminants until it is below the acceptable level.

In general, according to another aspect, the invention features a method for identifying bacterial species comprising growing a bacterial culture in a sealed container, detecting an absorption spectra of a gaseous headspace of the sealed container using a quantum cascade laser spectroscopy system, identifying a gaseous composition of the headspace by analysis of the absorption spectra, and correlating the gaseous composition of the headspace with a presence of a specific species of bacterium.

In general, according to another aspect, the invention features a method for monitoring biological or chemical reactions comprising connecting a quantum cascade laser spectroscopy system to a fiber optic probe, placing the fiber optic probe in contact with a chemical or biological reaction, detecting an absorption spectra of the reaction at multiple time points, comparing the absorption spectra to a standard, and determining the rate of the reaction.

In general, according to another aspect, the invention features a method for distinguishing between cell types in vivo, comprising connecting a quantum cascade laser spectroscopy system to a fiber optic probe, placing the fiber optic probe in contact with cells of a patient, scanning the cells with the fiber optic probe, recording the absorption spectra of the scanned cells, comparing the spectra to a library of spectral data, and determining cell type as a function of the spectral data.

In general, according to another aspect, the invention features a method for testing composites for thermal damage comprising: detecting an absorption spectra of a composite using a quantum cascade laser spectroscopy system, and identifying damage to the composite by comparison of the absorption spectra to the spectra of the same composite without thermal damage.

In general, according to another aspect, the invention features a spectroscopy system comprising: an external cavity laser including a laser cavity, a quantum cascade gain chip for amplifying light within the laser cavity, and a tuning element for controlling a wavelength of light generated, wherein the tuning element is resonantly tuned to scan the wavelength of the light, a sample detector for detecting the light returning from a sample, and an accumulator that stores the instantaneous response of the sample detector in a bin corresponding a wavelength of the light.

In general, according to another aspect, the invention features a method for identifying chemicals on reflective surfaces comprising directing emission from a quantum cascade laser spectroscopy system towards a reflective surface at a stand-off distance, detecting an absorption spectra of the reflective surface using the quantum cascade laser spectroscopy system, comparing the absorption spectra with a spectral data library, and identifying any chemicals on the reflective surface.

In embodiments, the Kramers-Kronig (KK) transform is applied to the absorption spectra to remove specular distortions.

In general, according to another aspect, the invention features a method for identifying chemicals in pools of liquid comprising: directing emission from a quantum cascade laser spectroscopy system towards a pool of liquid on a surface at a stand-off distance, detecting an absorption spectra of the pool of liquid using the quantum cascade laser spectroscopy system, comparing the absorption spectra with a library of spectral data, and identifying any chemicals present in the liquid.

The above and other features of the invention including various novel details of construction and combinations of parts, and other advantages, will now be more particularly described with reference to the accompanying drawings. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 34-37 are schematic diagrams shows implementation of the probe;

FIG. 41 is a flow diagram illustrating algorithm methodology for identifying substances using the QCL spectroscopy system.

DETAILED DESCRIPTION OF THE PREFERRED EMBODIMENTS

Figure 1:
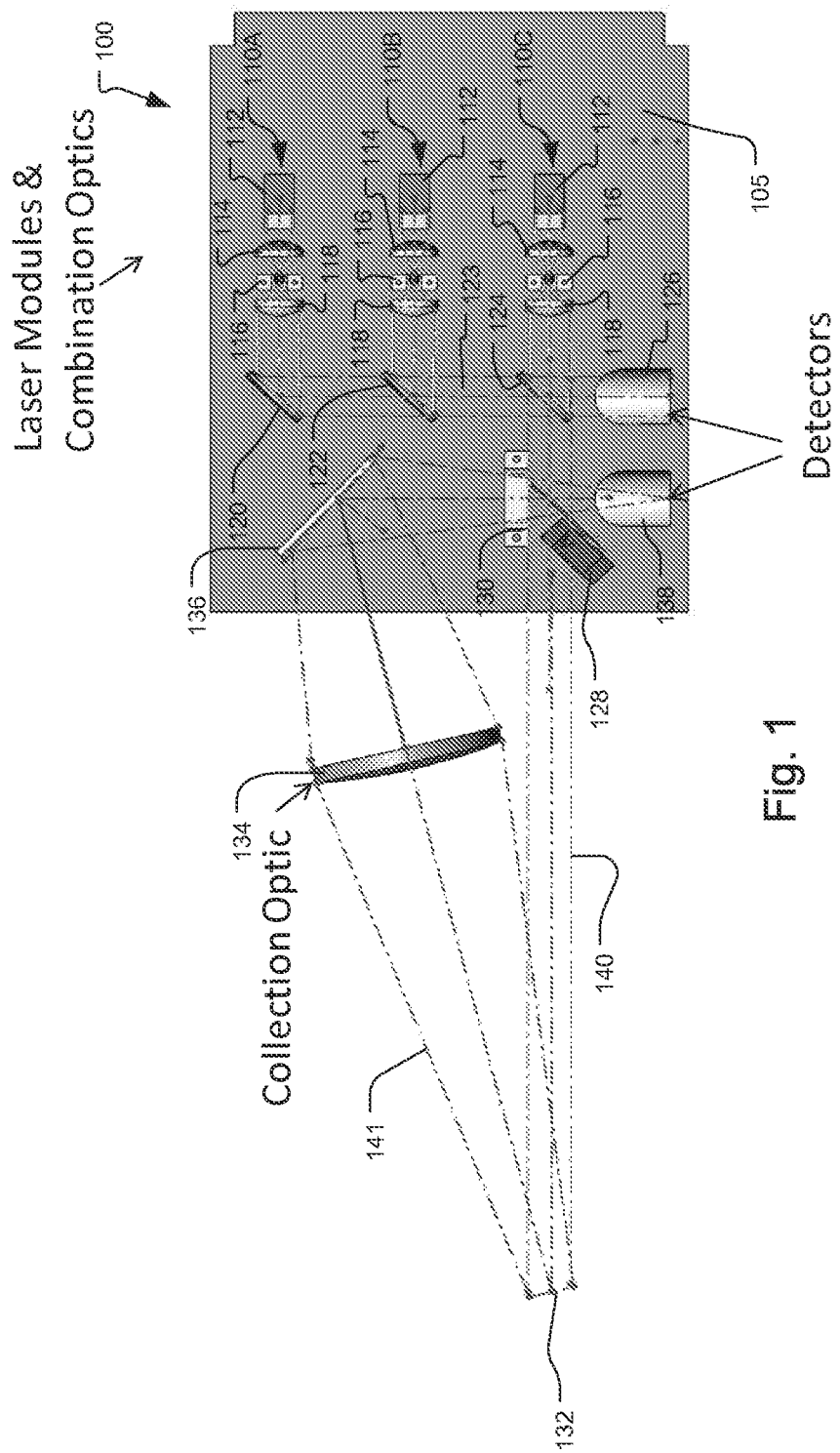
FIG. 1 is a scale plan drawing of a QCL spectroscopy system of the present invention.

The system that is described herein is a Mid-IR Tunable Quantum Cascade Laser (QCL) based spectroscopy system. This system is capable of obtaining absorption spectra of various materials for identification and analysis. It operates by emitting a wavelength range that is within the mid-IR fingerprint region (1500-900 cm-1) in a continuously or discretely tuned repeating packet. In one embodiment, the system has measurement range of 6 to 12 micrometers, with current versions offering 6 to 10 micrometers and 7 to 12 micrometers.

Traditionally, these types of measurements have been taken utilizing Fourier transform infrared (FTIR) spectrometers working the mid-IR. An FTIR spectrometer typically utilizes a broadband mid-IR source such as a heated black body source and a Michelson interferometer.

In contrast, the current system takes the same spectral measurements with a tunable mid-IR laser and detector that correlates the output signal with the signal that is returned from the sample. Because the laser can illuminate the sample with much higher power than the glowing black body source of the FTIR spectrometer, there are several key advantages that this system has relative to an FTIR spectrometer. These advantages include: faster measurements, more sensitive measurements due to higher signal to noise ratios, and sensitive standoff measurements where measurements are taken of trace substances at a distance.

The combination of three key independent innovations enable QCL based spectroscopy systems to take sophisticated spectral measurements. They include:

1. A widely tunable spectral range QCL assembly tunes across the mid-IR fingerprint spectral range, such as 6 to 12 micrometers. Previously, QCLs have been utilized in relatively narrow tuning ranges and have not been packaged together into a system that provides sufficiently wide ranges to perform sophisticated spectral measurements. The described system includes multiple laser tuner packages that are optically aligned to emit from the same exit optics and their emissions stitched together, spectrally, to achieve both a continuous and a wide tuning range.

2. Very rapid and repeatable laser pulses are tuned across the mid-IR fingerprint region. It provides high levels of repeatability in the amplitude of tuning range (good 100% line), low noise, rapid tuning, and a compact device.

3. Very fast electronics correlate the return signal with the emitting wavelength, so that it is possible to reconstruct the absorption spectra. The absorption spectra are produced after either averaging or in near real-time.

The following provides more details on each of these three key innovations:

Widely tunable QCL Laser Assembly

The described system includes multiple laser tuner packages that are optically aligned to emit from the same exit optics and their emissions stitched together to achieve both a continuous and a wide tuning range. Each of the laser modules is combined together using a combination of mirrors and dichroics, so that all of the beams exit through the same laser output port. Each of the modules independently covers at least 100 wavenumbers and usually covers 200 wavenumbers or more, in embodiments. The system with multiple modules combined together provides sufficient spectral range to do practical absorption spectroscopy.

Furthermore, these laser modules either scan through their complete spectral range in sequence or their pulses are interleaved. When the tuners are interleaved, during the time that the first laser fires and then turns off, the second laser fires and turns off, then the third laser fires and turns off, and then repeats with the first laser firing again. The advantage with interleaving is that it takes advantage of the downtime in the duty cycle of each laser to minimize the time required to cover the full spectral range of all of the laser packages combined.

FIG. 1 shows a QCL spectroscopy system 100 which has been constructed according to the principles of the present invention.

It comprises an optical platform 105. Installed on the optical platform 105 are multiple tunable QCL lasers 110A, 110B, 110C. In other embodiments, more than three are installed together on the common optical platform 105.

The system in one example provides a nominal measurement range or scanband of 6 to 12 micrometers. Narrow scanning versions cover scanbands of 6 to 10 micrometers and 7 to 12 micrometers, however.

Each of the QCL lasers 110 includes a grating tuner 112. A QCL chip 116 is installed on a submount. An external cavity lens 114 couples light from the back facet of the QCL chip 116 to the grating tuner 112. Light exiting the front facet of the QCL chip 116 is collimated by an extraction lens 118.

The emission from the first QCL laser 110A is reflected by a fold mirror 120. A dichroic mirror 122 is reflective for the scan band of the second laser 110B but transmissive for the scan band of the first QCL laser 110A and it is angled at 45 degrees with respect to the tunable signals of both the first QCL 110A and the second QCL 110B. This generates a first combined beam 123 including the tunable signals from the first QCL 110A and the second QCL 110B. The combined beam 123 from the first and second QCL lasers is directed at a partially reflecting mirror 124. The emission from the third QCL laser 110C is directed at the same partially reflecting mirror 124, with the partially reflecting mirror 124 being angled at 45 degrees with respect to both the first combined beam 123 and the tunable signal from the third QCL 110C. This results in a final combined beam 140 is that includes the signals from all three QCL lasers 110. Similarly, the emission from all three QCL lasers is also received by a reference detector 126 located opposite to the partially reflecting mirror 124.

In other embodiments, element 124 is a dichroic mirror that is reflective in the scan bands of QCL's 110A and 110B but transmissive to the scan band of QCL 110C. In this case some residual light from all three QCL's still reaches the detector 126.

The combined output beam 140 exits through an optical port and is directed at the sample 132. In a typical application, the sample 132 diffusely or specularly reflects the output beam 140. This light 141 is collected by a large collection optic 134 and coupled back to the optical platform 105. The light is reflected by a fold mirror 136 on platform 105 and is detected by a sample signal detector 138.

A spectroscopy reference or gold coated wafer 128 is installed on an actuator arm 130. During a calibration process, this spectroscopy reference 128 is inserted into the output beam 140 to reflect the output beam 140 to the sample detector 138. This allows for the calibration of the sample detector 138.

Figure 2:
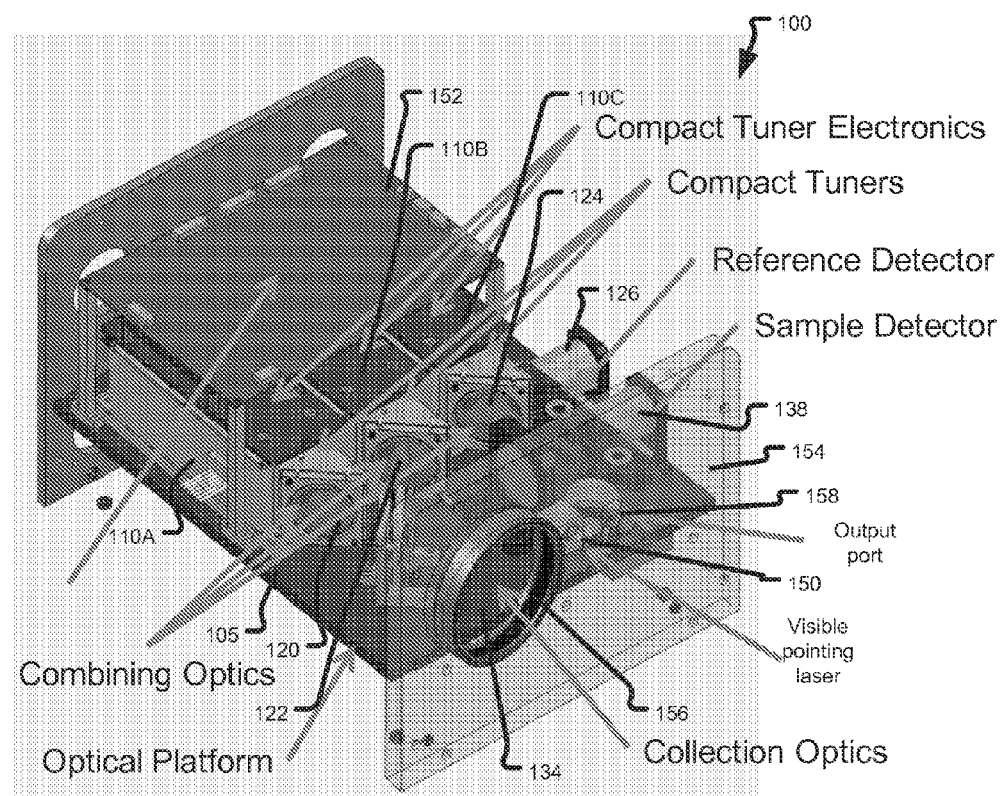
FIG. 2 is a scale perspective drawing of a QCL spectroscopy system of the present invention showing parts of the housing and electronics boards.

FIG. 2 is a perspective view of the QCL spectroscopy system. It shows the optical platform 105 with the combining optics including the fold mirror 120, dichroic mirror 122, and partially reflecting mirror 124. Also shown is the reference detector 126 and sample detector 138. The compact QCL tunable lasers 110A, 110B, 110C are installed on a line underneath the tuner electronics board 152. Also shown in the front panel 154 of the system 100 with the collection optics port 156, the output port 158 and a pointing laser 150 generates a visible spot that coincides with the non-visible emission through the output port 158.

Figure 3:
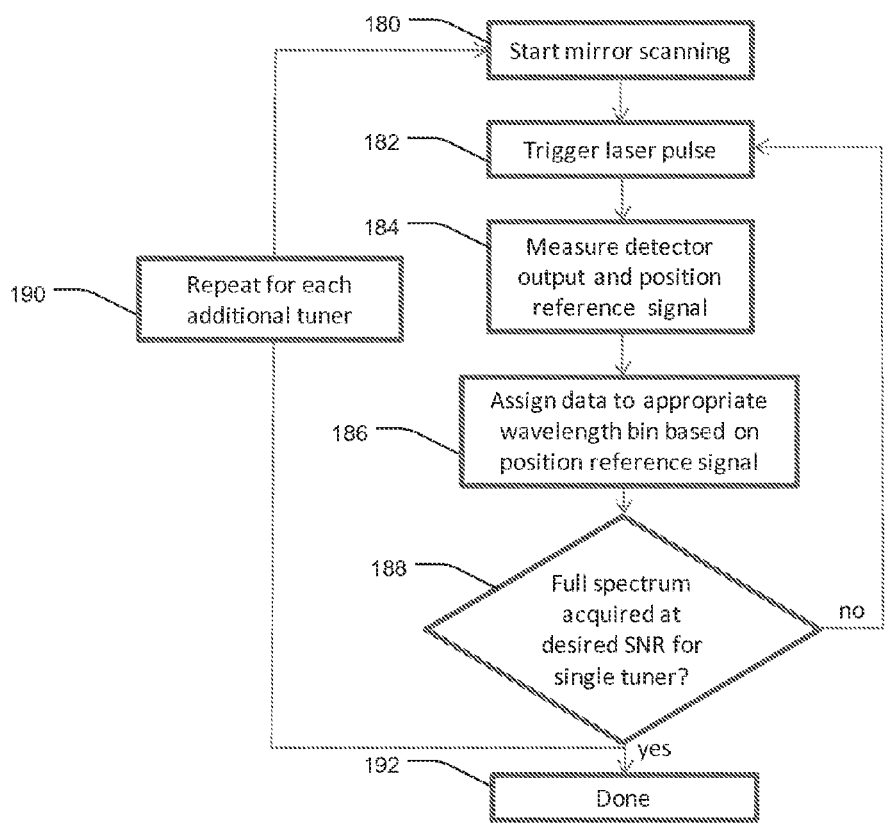
FIG. 3 is a flow diagram illustrating one mode of operation for the QCL spectroscopy system for non-interleaved spectral acquisition.

FIG. 3 is a flow diagram illustrating one mode of operation for the QCL spectroscopy system 100 for non-interleaved spectral acquisition. In this operation, the QCL tunable lasers 110A, 110B, 110C are operated in a serial fashion.

In more detail, in step 180, the mirror or grating of one of the tuners is started to scan. This causes the emission or tunable signal of the QCL 110 to spectrally scan over its scan band. The electronics trigger the laser pulse in step 182. Then the reference detector 126 measures the wavelength of the emission in step 184. The resulting data detected by the sample detector are assigned to a wavelength depending on the wavelength detected by the reference detector 126 or based on the position of the grating tuner 112.

In step 188, it is determined whether a full spectrum at the desired signal-to-noise ratio has been captured for the tuner. If not, then the process repeats. If adequate spectrum has been captured, the process repeats for the next tuner in step 190. In this way, a spectrum is accumulated for the scan band of each tuner until an entire spectrum has been captured in step 192.

Figure 4:
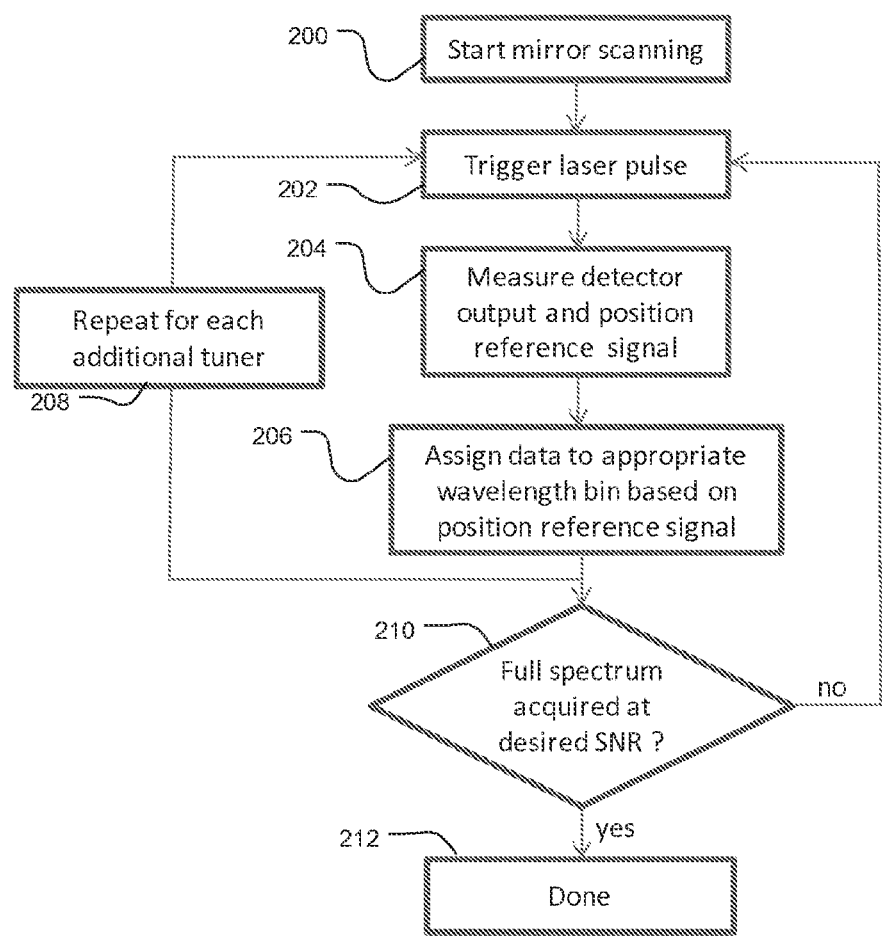
FIG. 4 is a flow diagram illustrating operation for the QCL spectrally spectroscopy system for interleaved spectral acquisition.

FIG. 4 is a flow diagram illustrating another mode of operation for the QCL spectrally spectroscopy system for interleaved spectral acquisition.

In this example, all of the grating tuners 112 of the QCLs 110 are triggered to start scanning in step 200. Then, a trigger pulse is issued to one of the tuners 110 in step 202. The reference detector 126 determines the wavelength of the emission or the wavelength is determined by the position of the grating in the grating scanner 112. The signal detector 138 detects the response of the sample in step 204. The spectroscopy data are then assigned to the appropriate wavelength in based on the response of the reference detector or the position of the grating tuner in step 206. This process is repeated for the next tuner in step 208. In this way, each of the tuners detects the spectral response at a different point. In one specific example, the QCLs 110 take turns generating a single pulse serially with this process repeating until an entire spectrum has been acquired at the desired signal-to-noise ratio in step 210. Then the process completes in step 212.

Figure 5:
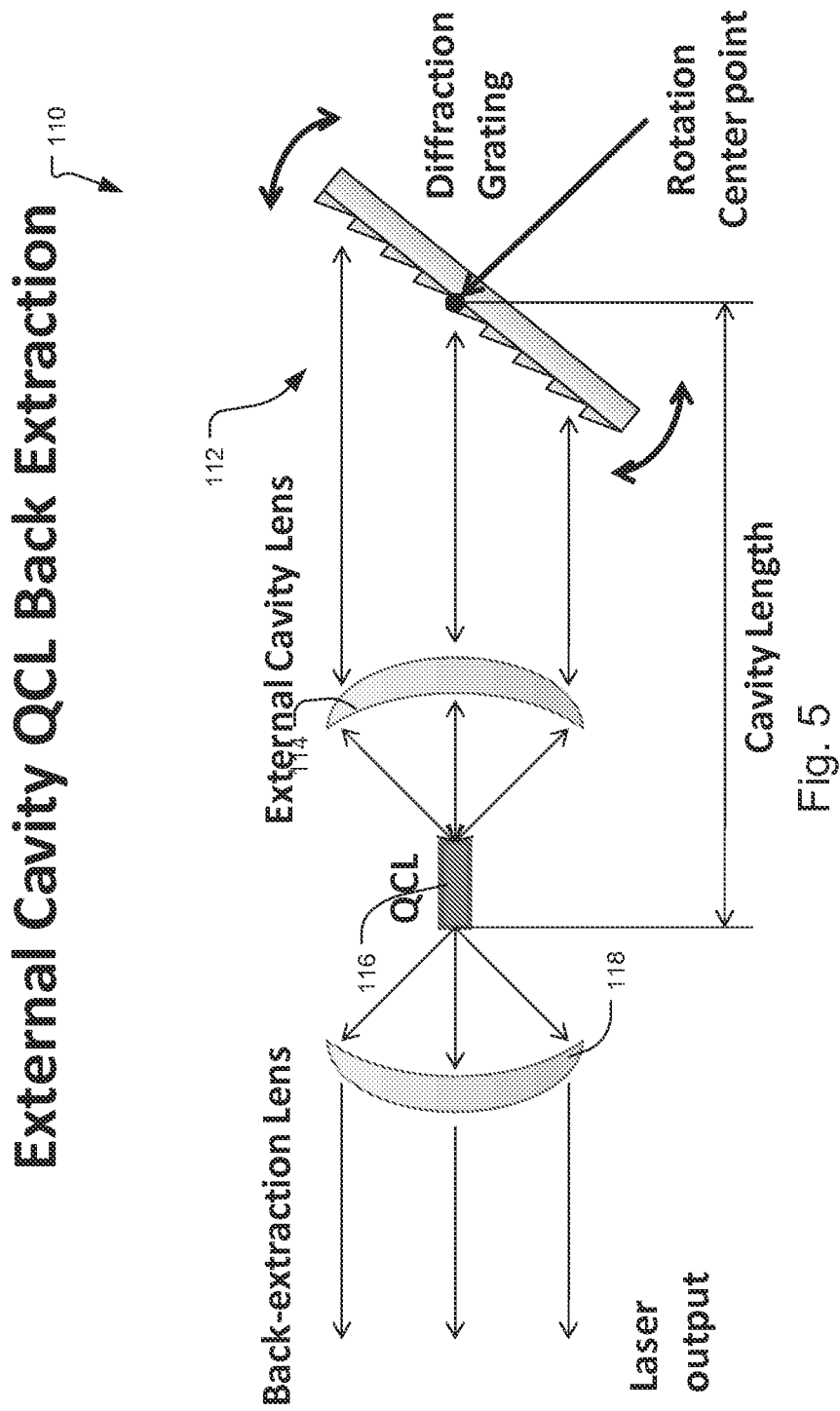
FIG. 5 is a detailed view showing one configuration for the external cavity configuration of the tuners 110.

FIG. 5 is a detailed view showing one configuration for the external cavity QCLs 110. In this example, the back facet light from the QCL 116 is coupled via the external cavity lens 114 directly to the diffraction grating of the grating tuner 112. The grating rotates around a rotation centerpoint. This changes the light that is reflected back to the QCL chip 116.

Figure 6:
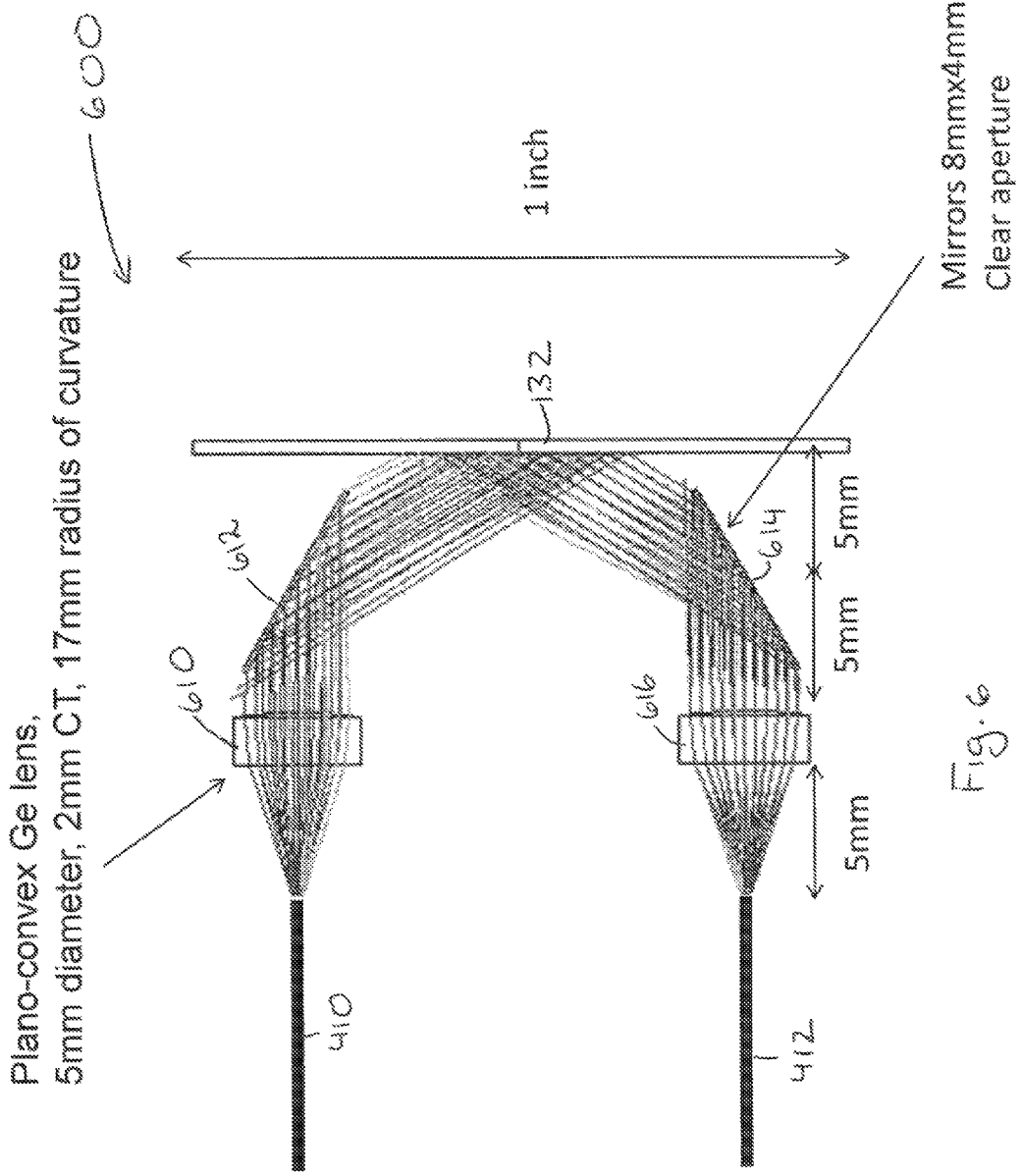
FIG. 6 is a detailed view of a grazing angle probe.

FIG. 6 is a view of a grazing angle probe which is connected to the QCL spectroscopy system 100 in one embodiment.

In more detail, the grazing angle probe is coupled, via fiber optic cables 410 and 412, with a widely tunable QCL spectrometer 100. The IR light generated from the QCL's 110 passes from the fiber optic cable 410 through a plano-convex Ge lens 610 and is directed to the sample 132 by a mirror 612. A second mirror 614 then directs the light through a second plano-convex Ge lens 616 to a return fiber optic cable 412, which transmits the light to the sample detector 138.

Resonant Scanning

Conventionally a laser can be tuned by rotating a grating, so that the first order of the grating is reflected into the external cavity. As the mirrored grating is rotated, a different wavelength is selected that is reflected into the cavity and amplified. The constraints on a system like this include that the size of the assembly and is dependent upon the size, weight, and speed of the affiliated actuator that is utilized to rotate it.

One embodiment avoids these constraints by keeping the grating fixed, but scans the laser beam across the grating utilizing a compact rotating mirror. The advantages of this approach includes size, because the mirror can be made very compact using conventional techniques and even smaller with microelectromechanical system (MEMS) technology. The mirror is scanned across the grating very quickly. It accomplishes a full wavelength scan in 1-10 milliseconds (msecs) or less, in one implementation, as opposed to the seconds required to move the much bigger grating. The entire assembly is much simpler because the mechanics and grating are decoupled and the mechanics to rotate the much smaller scanning mirror is not nearly as complex as what is required to move the bigger grating. Furthermore, the range of motion required on the mirror is half of what was needed for the grating.

The key elements of this system include a broadband QCL laser chip within an external cavity tuner that includes a high numerical aperture (NA) coupling lens that collimates the laser beam onto the mirror, which then scans the grating. The light is reflected back into the semiconductor chip at a specific wavelength, which causes the laser to lase at the desired wavelength. The laser light is then collimated by the high NA output lens, which creates the output beam.

Approximately 11 degrees of motion are required to scan a sufficient distance across the grating in order to reflect back light of 6 to 10 micrometers.

Figure 7:
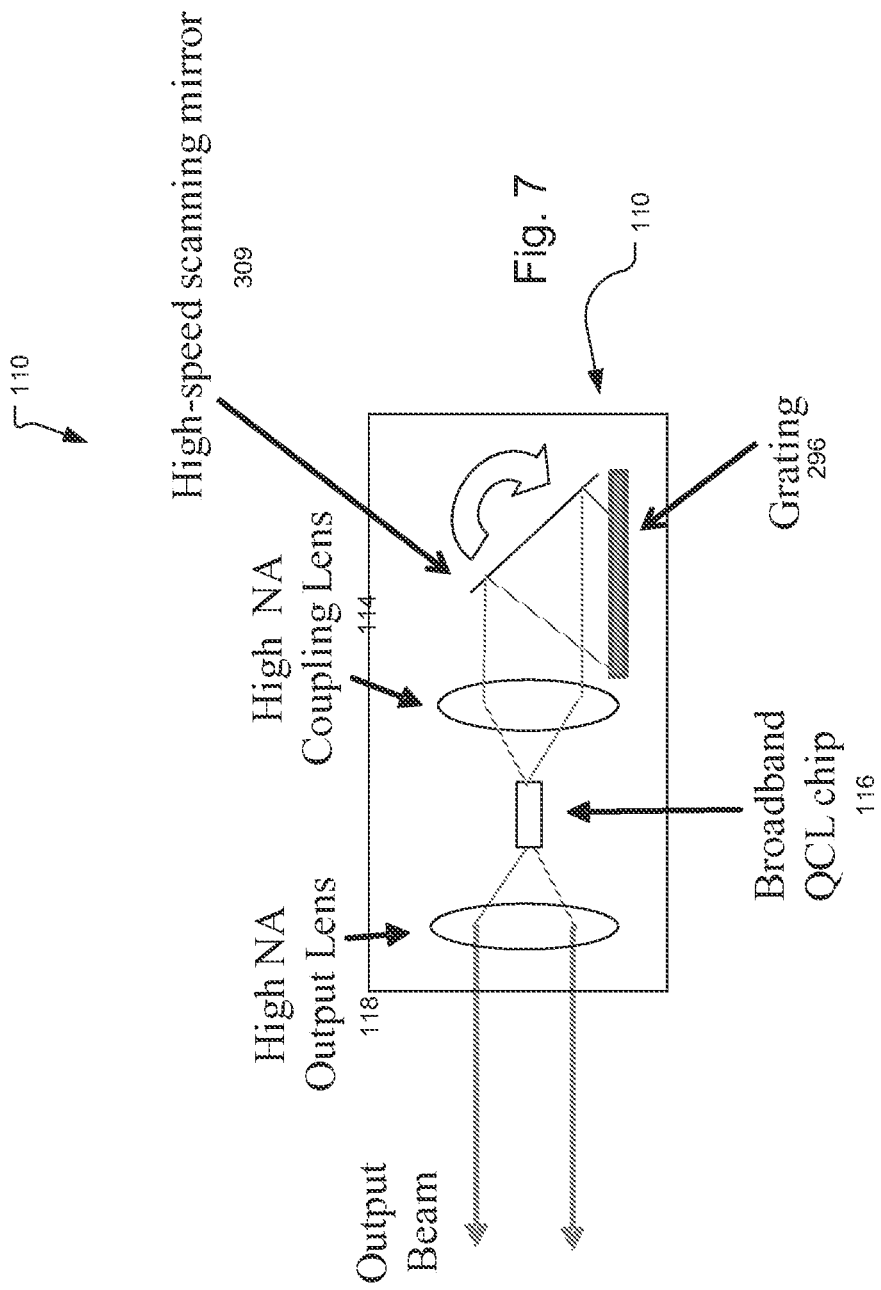
FIG. 7 is a detailed view showing another configuration for the external cavity grating tuner 110.

FIG. 7 is a detailed view showing a configuration for the external cavity QCL 110 using the resonant scanning system. This example uses a stationary grating 296. Instead, a high speed scanning mirror 309 is used to couple light in the external cavity between the grating 296 and back into the QCL chip 116. In the preferred embodiment, the scanning mirror 309 is a resonant scanning mirror that is low mass and scans at high speed. In this embodiment the relatively more massive grating 296 is stationary and only the lightweight mirror 309 scans. As a result, it is possible to make a small, light scanning mirror 309 using MEMs technology that is high speed such that a full wavelength scan is possible in 1-10 msec if SNR is adequate. Also assembly is simplified since scanning mechanics and grating are decoupled. Finally, the angular range of motion for the mirror 309 is half of that for the grating in the other configuration.

Resonant Scanner Spectral Sampling and Sorting

Because the time between laser pulses is long relative to the speed of the mirror 309, it is impractical for the mirror 309 and the pulses of the laser to be synchronized to provide a continuous sweep of the spectral range. Additionally, it would require a sophisticated timing system for the wavelength of any specific pulse to be pre-determined.

A more elegant approach is to pulse the laser, as the mirror moves. Then the position of the mirror 309 is determined using one or more of the following: position feedback signal, the drive signal (the voltage signal that is used to drive the mirror), or the clock signal (one round trip of the mirror is a single clock cycle). The position of the mirror indicates which part of the grating 296 the beam is illuminating, which is translated into an approximate wavelength via a lookup calibration table, for example. In another example, a reference detector system is used that resolves the instantaneous wavelength of the tunable signal from the tunable QCL system.

The spectral range is divided into a number of bins. The signal detected from the sample for each of the laser pulses is placed in a bin, based on its calculated wavelength. As the mirror continually scans and the laser pulses, new wavelength measurements are taken. The pulsing continues until enough samples have been taken per bin to provide a spectrum of the measured sample. The resolution of this spectrum is based on how many bins the range is divided into.

A side-effect from the sinusoidal motion of the mirror 309 is that the spectral distribution of the samples are grouped at the end of the spectral range.

Figure 8:
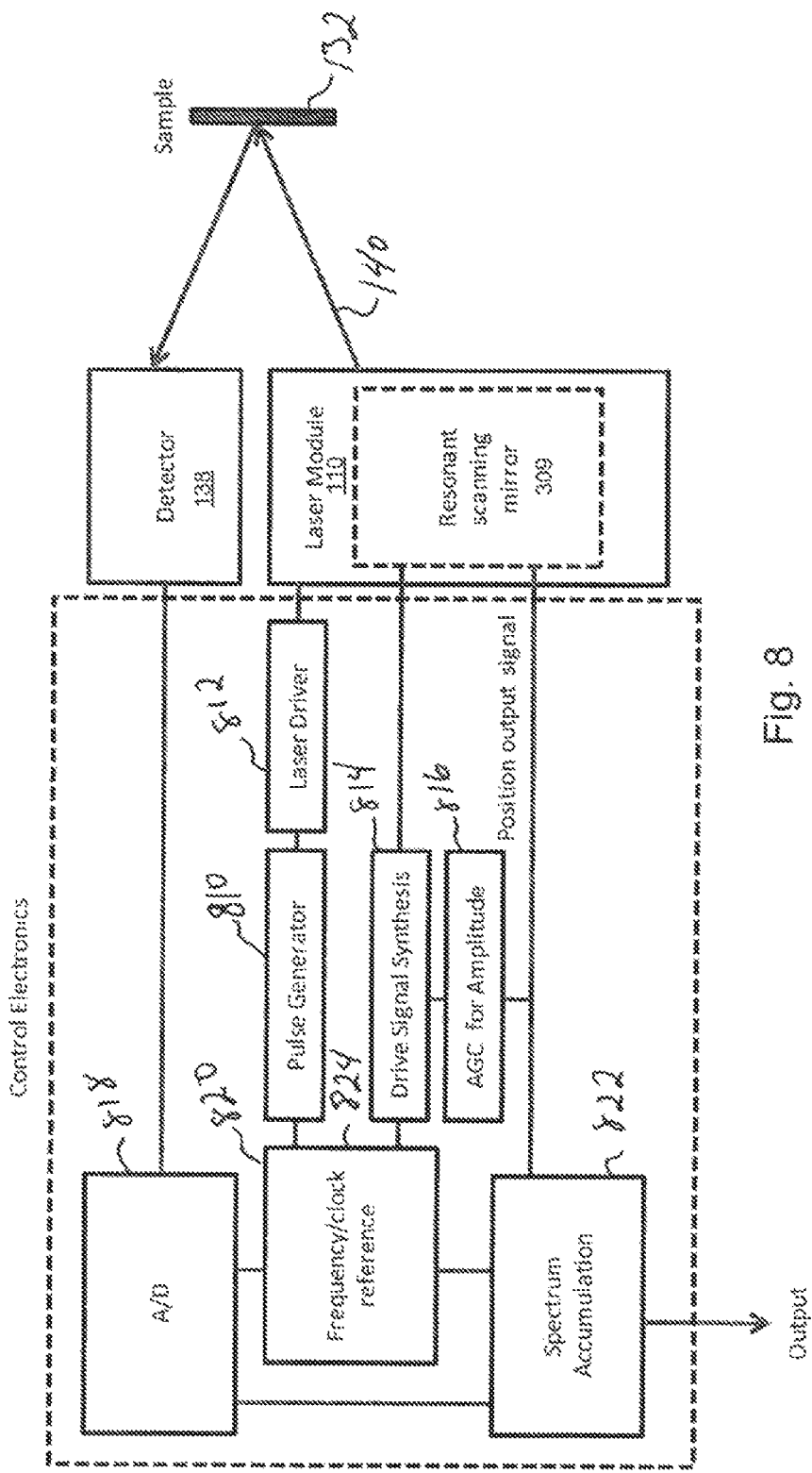
FIG. 8 shows the electronics for the QCL spectroscopy system using the resonant scanning mirror.

FIG. 8 shows the electronics for the QCL spectroscopy system. In more detail, one or more laser modules 110 with their respective resonant scanning mirrors 309 are used to generate the tunable signal 140 that it is spectrally scanned over the sample 132. The laser modules 110 are driven by a pulse generator 810 through a laser driver 812. A drive signal synthesis system 814 controls the resonant scanning mirrors 309 of the QCLs 110. An automatic gain control circuit 816 is used for amplitude and to obtain the position output signal. This position output signal corresponds to the current position of the scanning mirror and thus directly corresponds to the wavelength of the tunable signal 140. The sample detector 138 is monitored by an analog to digital converter 818. This provides digital data to a spectrum accumulation system 822. In more detail, the spectrum accumulation system 822 stores the instantaneous response of the detector and the corresponding wavelength as dictated by the position output signal. A clock reference 824 synchronizes the pulse generator 810 and the drive synthesis system 814 and triggers the acquisitions by the analog digital converter 818.

Figure 9:
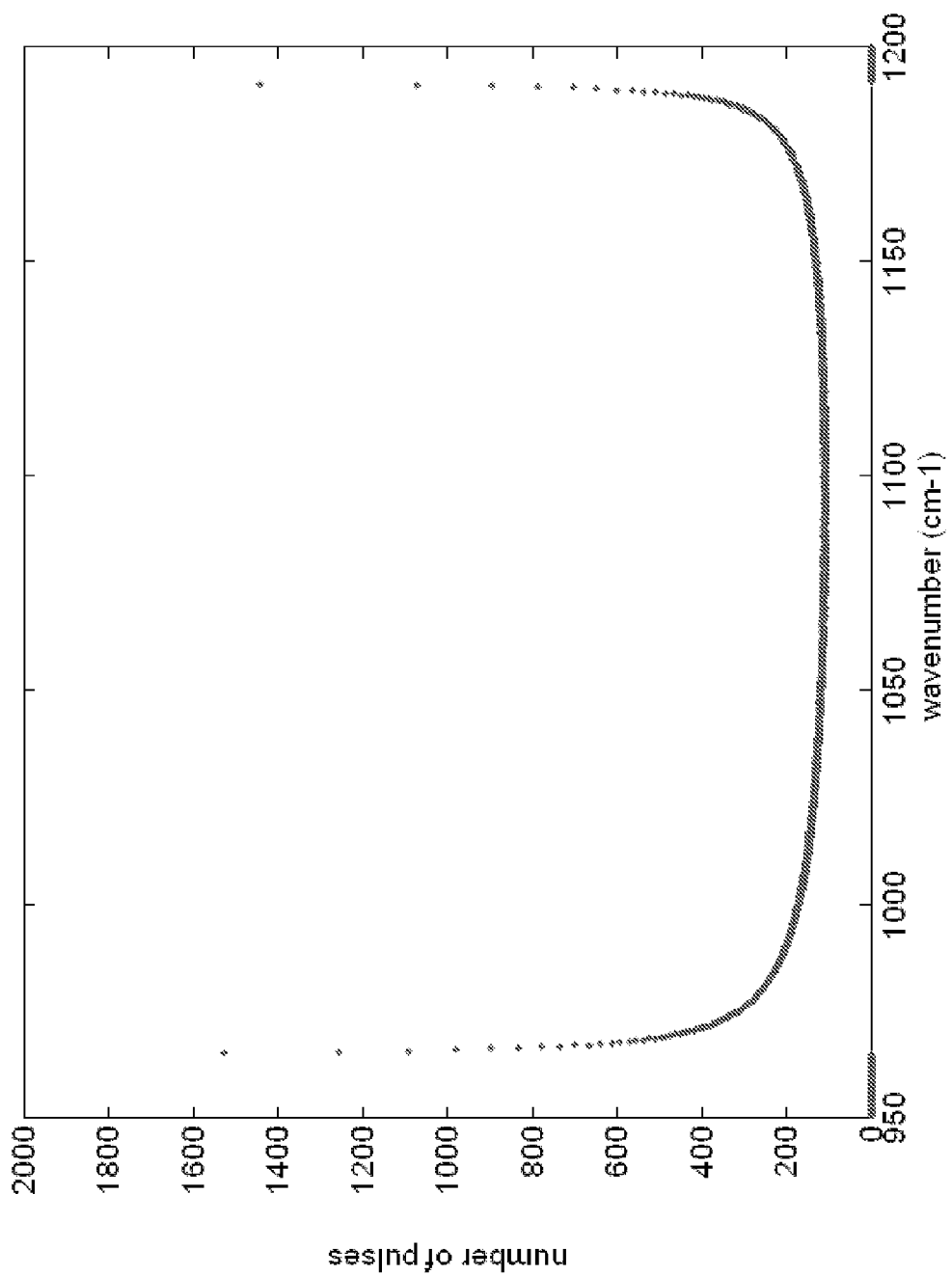
FIG. 9 is a plot of pulses as a function of wave number generated for the resonant scanning grating tuning system.

FIG. 9 is a plot of pulses as a function of wave number. The plot shows number of pulses per 0.2 cm-1 frequency bin for 1 sec total scan with pulse frequency of 200 kHz and scanner frequency equal to 110.0108 Hz. In one example, the minimum number of pulses in any bin=114. The scan amplitude is set to cover the range from 970 to 1190 cm-1. Spectrum is sampled at different points on each scan until a spectrum is accumulated. Generally, we want a maximum of about 1000 bins per tuner 110.

Figure 10:
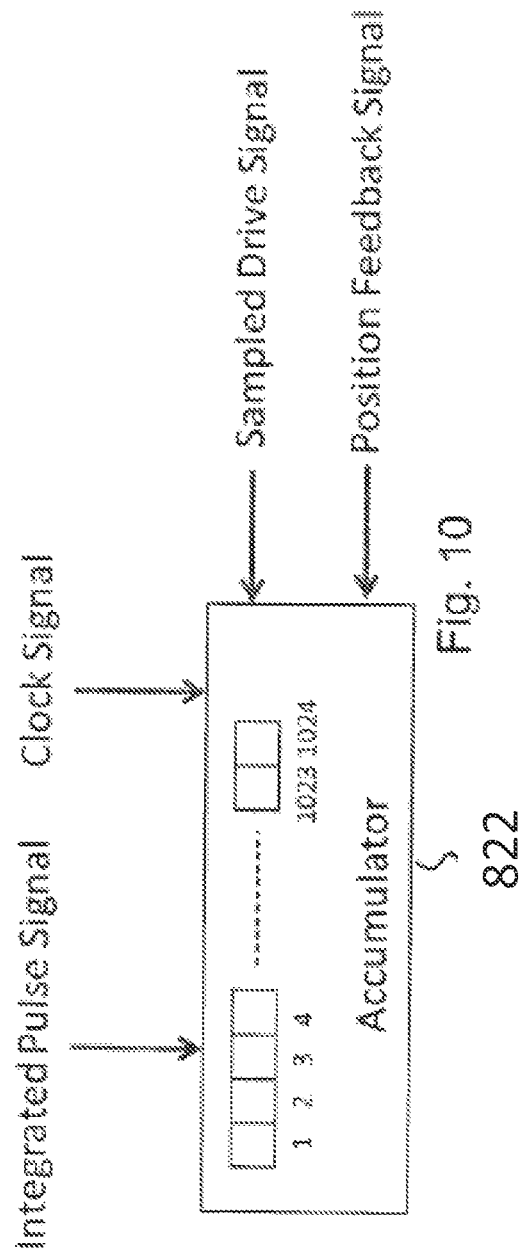
FIG. 10 shows the electronics that enable the integrated pulse data to be sorted into spectral bins.

FIG. 10 shows the electronics that enable the integrated pulse data to be sorted into spectral bins. In the illustrated example, a 1000 bin accumulator functions as the spectrum accumulation unit 822. Each bin accumulates the response associated with a different range of wavelengths within the scanband of the system 100. It stores the integrated pulse signals from the A/D converter 818 in response to the clock signal from the frequency/clock reference circuit 824. The data are stored into one of the bins based upon the sampled drive signal or a position feedback signal for the resonant scanning mirror 309, which indicate the instantaneous wavelength or wavenumber of the tunable signal 140. In other embodiments, the bin is determined with respect to the output of a reference detector that determines the spectrum of the signal from the spectroscopy system.

Additionally, comparison of the position feedback signal with the drive signal can be used to detect any anomalies in the motion (from shock and vibration, for example). A decision to ignore potentially bad data or to re-scan is preferably made based upon this information.

Processing

A laser pulse is triggered by the electronics at a specific wavelength. Then when the light is reflected back from the sample 132 to the sample detector 138, the wavelength of light is correlated with the amplitude of the signal on the detector. This process is repeated numerous times to build up a full spectrum of absorption data. The key to this processing allows the system to use a pulsed tunable laser to build up spectrum comparable to what one would get with an FTIR spectrometer.

One of the keys to pulse processing is the detector is sampled at discrete intervals, in order to avoid confusing background energy with the reflected pulse energy. When the laser is dormant it is possible to obtain a baseline energy, so that the integrated pulse energy stands out from the background. The sum of the samples during a baseline region is subtracted from sum of samples during pulse integration region to give an integrated pulse energy for the pulse.

Figure 11:
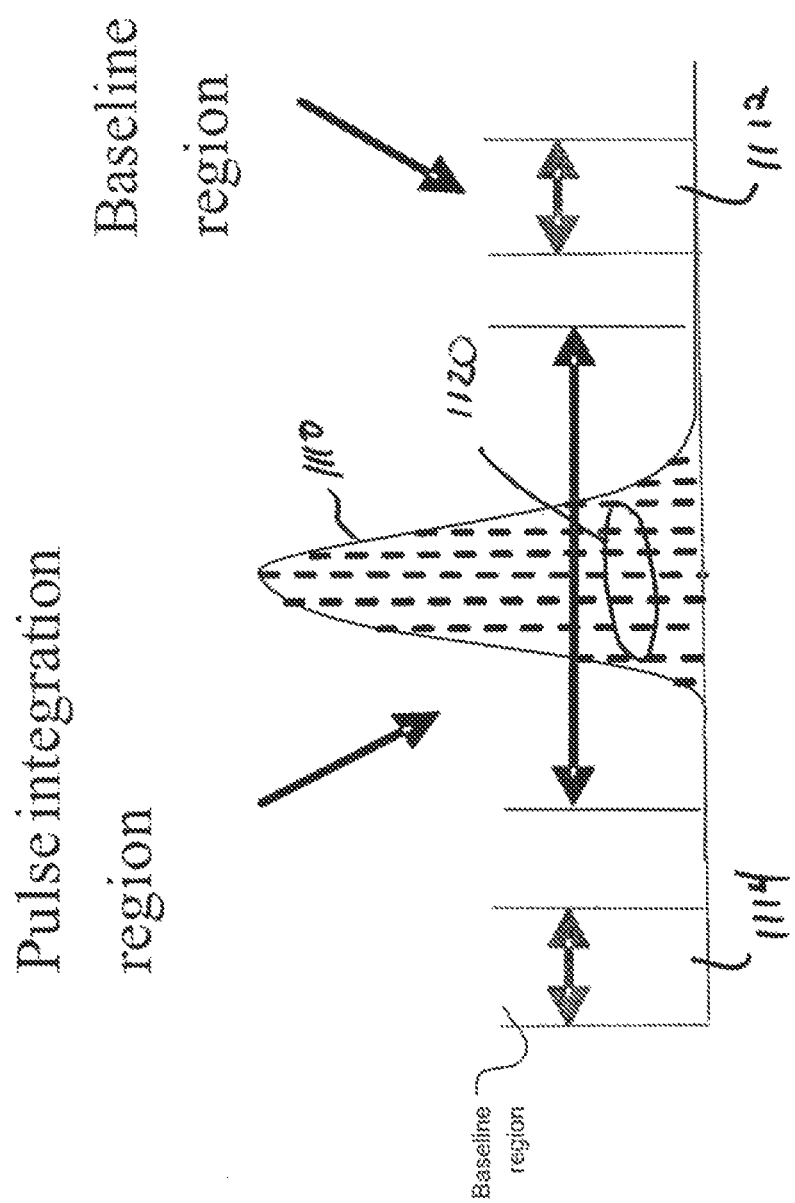
FIG. 11 illustrates the temporal sampling of the sample detector relative the pulse generated by the QCL.

FIG. 11 illustrates the sampling of the sample detector 138 relative the pulse 1110 generated by the QCL tuners 110A-110C. The sample detector 138 is sampled at discrete intervals such as 5 to 10 or more during each pulse integration region 1110. The sample detector 138 is also sampled before and after the pulse region in order to get a baseline level 1112, 1114. Sum of samples 1120 during baseline region is subtracted from sum of samples during pulse integration region 1110 to give integrated pulse energy.

Figure 12:
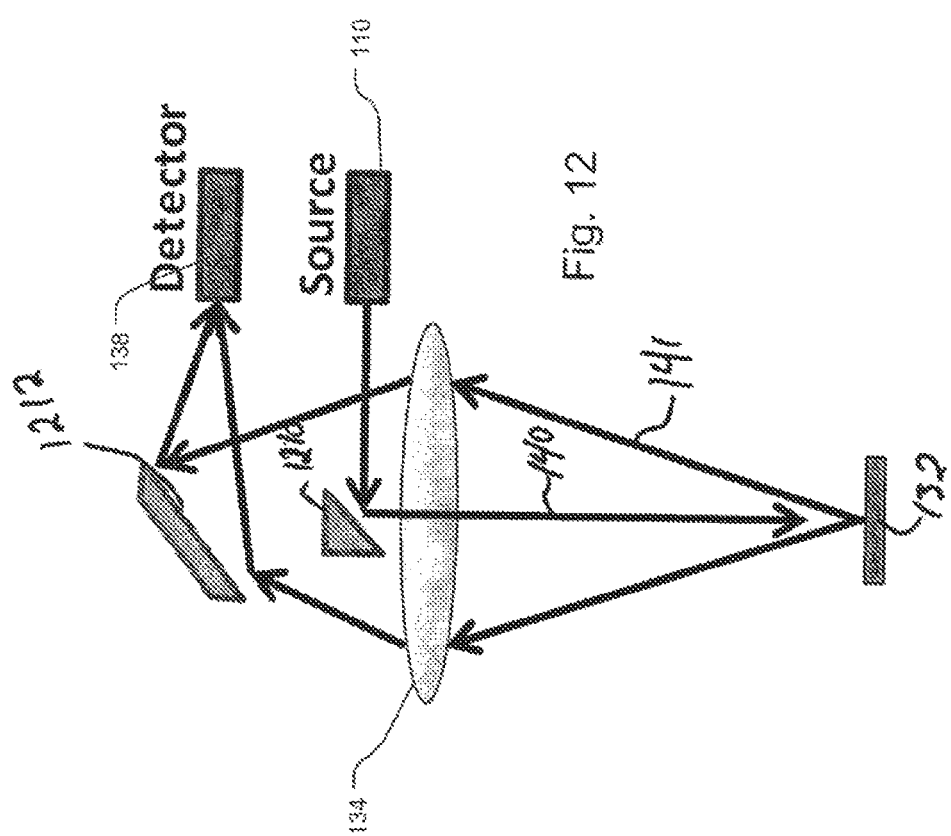
FIG. 12 illustrates an alternative optical train design.

FIG. 12 illustrates an alternative to optical train design. In the optical train illustrated in FIG. 1, the illumination beam from the tuners 110 is off axis with respect to the axis of the collection optics 134. In contrast, FIG. 12 illustrates a collinear design. In more detail, the tunable signal 140 from the tuners 110 is reflected by a fold mirror 1210 to pass through the center of the collection optics 134 to the sample 132. Light 141 returning from the sample 132 is then collected by the collection optics 134 and coupled to the sample detector 138 by a second fold mirror 1212.

Three main practical applications of the QCL spectroscopy system 100 will now be presented. These applications can broadly be defined as using the QCL spectroscopy system 100 for standoff detection, using the QCL spectroscopy system 100 with probes for near-range observation, and microscopy using the QCL spectroscopy system 100. All three of these applications demonstrate novel ways in which the QCL spectroscopy system 100 provides significant improvements over existing technology.

Standoff Measurement with the QCL Spectroscopy System

Figure 13:
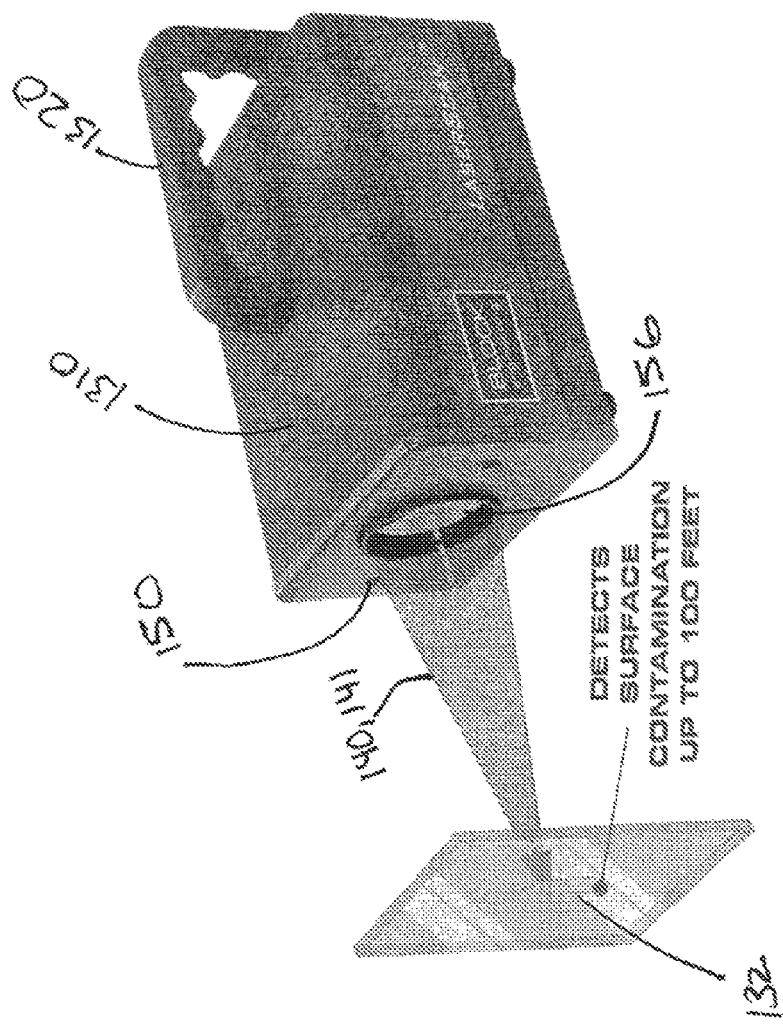
FIG. 13 shows a portable configuration of the QCL spectroscopy system.

FIG. 13 illustrates a portable embodiment of the QCL spectroscopy system 100 allowing handheld remote inspections of surfaces at varying distances. In this embodiment, the QCL spectroscopy system 100 is contained within in a housing 1310 having a handle 1320 for greater portability. With this configuration materials are analyzed on surfaces, and this measurement is usually made from several feet away from the subject or sample (typically 3 to 5 feet) and up to very remote distances, such as 100 feet. A red (visible) sighting laser 150 is included to help the user locate the correct sampling point, remembering that infrared laser radiation is not visible to the human eye. Upon projection, the infrared sample beam 140 is set to 4 millimeters (mm) in diameter. The user does not have to worry about scattered radiation from the laser because the beam is eye-safe. The large IR collection optic 156 provides efficient light collection from a remote sampling point 132. Alternative embodiments of the system include a laboratory oriented configuration that enables the use of standard FTIR accessories. In this mode of operation, standard IR cells, reflectance accessories, and even microscope accessories can be accommodated.

The portable embodiment of the QCL spectroscopy system 100 described above allows handheld remote inspection of surfaces at varying distances. In order to enable this mode of operation the co-linear optical arrangement shown in FIG. 12 is used where the laser illumination path 140 follows directionally the same effective path as the returning reflected beam 141. This allows the instrument to be used from distances of a few inches to several feet from the sample surface, making it ideal as an inspection tool or as a stealth or non-contact tool for the detection of materials on surfaces for law enforcement or security applications. Applications in this mode of operation are featured below.

Stand-Off Applications of the Tunable QCL Spectrometer

Fundamentally, a broadly tunable QCL spectrometer 100 functions as any other infrared spectrometer. It may be used in a laboratory environment for standard transmission measurements on solids, liquids and gases. The laser also inherently provides a high optical throughput, for trace monitoring applications, as well as for low level transmission or low reflectivity measurements, as experienced with highly absorbing sample substrates, or with micro-sampling methods.

One attribute utilized in a stand-off arrangement is the higher spectral power density (at a particular wavelength) at the sample; estimated to be one or two orders of magnitude greater, at a particular wavelength in time, than a traditional IR source as used in an FTIR. This increased performance is realized in terms of higher SNR (signal-to-noise ratio) for energy returning from remote surfaces. An added benefit for this application is the directional characteristics of the IR beam that results from physical characteristics of the laser source (beam coherence with a minimally divergent beam). This feature enables samples to be accurately targeted, and the minimum beam divergence ensures optimal coupling between the infrared beam and the remote sample.

The QCL spectrometer 100 is particularly useful in the area of remote or stand-off measurements. This mode of measurement is unique for routine sampling and is usually impractical with a conventional FTIR-based system. Reflectance measurements from surface with a conventional FTIR require a very close-coupled reflectance accessory where the distances are kept very small between the sample and the incoming focused sample beam, and where equally closely coupled collection optics are required to direct the beam efficiently back to the instrument's detector. This includes both specular and diffuse reflectance measurements. In both cases, the need to focus the beam on to the sample, and the need to collect a rapidly diverging beam (specular measurement) or a highly scattered beam (from a diffuse surface) limits the illumination and collection geometries to about a centimeter, at the very most. At larger distances, the ability to optimize the coupling of the focused beam is lost, and there is too much divergence or even scattering from the emergent beam to enable efficient light collection without the need of a very large optical system.

There are commercial instruments (FTIR and Raman) for handheld stand-off measurements and non-contact measurements of samples. These are limited to close-up measurements, where the spectrometer is used a few millimeters from the surface or for attenuation total reflection (ATR) based measurements where actual surface contact is required. While both of these approaches work, they have limitations, both in terms of basic performance, and in the case of ATR, where there is a high risk of contamination of the sampling head, and/or the sample surface. A stand-off measurement eliminates these problems and risks. QCL can be used for a complete remote stand-off measurement where accurate spectral data are acquired for materials on surfaces without the safety and/or contamination issues highlighted above.

While there are handheld FTIR spectrometers for the non-contact, remote/stand-off measurement of surfaces and for the characterization of materials on surfaces, these devices are constrained by distance from the subject. Typical stand-off distances for such measurements with an FTIR are a few millimeters to a centimeter or two (for a reflective surface) at best. Even in the laboratory, with a bench-top FTIR, reflectance measurements with standard accessories only allow a separation from the sample surface of about a centimeter or two. The directional properties of the laser, plus the higher spectral power density enable good quality spectra, comparable to laboratory quality FTIR spectra, to be obtained from surfaces at distances of one foot to six feet away from the subject, and up to 100 feet for truly remote applications. This opens up a range of new applications, not possible by FTIR, which include remote detection of explosives and chemical agents on surfaces (military and public safety), surface contamination measurements, and the determination of surface composition of non-accessible surfaces, which can include surfaces inside vessels or containers, surfaces in dangerous environments, and measurements from hot (high temperature) surfaces. The latter is an important consideration for process monitoring and catalyst surface study applications.

Stand-Off Measurement of Chemical Agents

As indicated, one area in which the QCL spectroscopy system 100 is particularly useful is in the stand-off measurement of chemical agents. Chemical agents can be measured whether present as a residue or thin films on a surface or in a pool of liquid.

When known chemical agents are present as a thin film or residue on a reflective surface, such as an aluminum surface, spectral data obtained by stand-off measurement with the QCL spectroscopy system 100 show a combination of reflection and transmission like spectra, resulting in mixed mode measurements for some samples. In spite of the mixed mode effects, the spectra are still unique and can be used, via comparative methods, to identify the agents.

A method for using the QCL spectroscopy system 100 to remotely measure contaminated reflective surfaces is useful in instances such as in military or public safety substance detection where the subject, with a painted metal surface, has residues of a common explosive. When spectra are compared for painted surfaces where one set of samples are laboratory prepared references recorded on a laboratory FTIR with the aid of a 30° angle of incidence reflectance accessory, and the other set contain explosive residues on the surfaces, measured by the QCL at a distance of about 5 feet, the spectra measured by the QCL will exhibit unique anomalous dispersion effects as typically observed in thin film reflectance spectra from highly absorbing substrate surfaces. From the point of view of characterization, these materials can be differentiated, even though they may be convolved with some of the spectral characteristics of the background or substrate. This format of spectrum can be used directly with a library of similarly recorded data for known substrate materials. If there is a requirement to compare the recorded spectrum with a standard library of spectra in transmittance or absorbance format, then the spectrum may be qualitatively compared to the library after a band inversion (for the transmittance format).

The traditional infrared measurement of liquid samples was by light transmission through the sample. Samples were measured as a liquid film between IR transparent windows. The stand-off measurement of chemicals in liquid form is more complex because the liquid has both transmissive and reflective properties. The stand-off analysis of liquids on surfaces requires the measurement of the IR light reflected either through or off the surface of the liquid.

If the liquid forms a thin film on the surface, such that the light passes through the liquid and is reflected back from the surface and the reflected light is measured, then a "transmission" spectrum is recorded. This mode requires that that the surface is reflective, such as an aluminum surface.

Reflection from an infrared absorbing surface, such as the liquid, is a complex function and is related to the refractive index of the material. The resultant specular reflective index spectrum correlates to changes in refractive index and provides a very different, derivative like spectrum.

If the light partially transmits through the liquid (in areas where the sample has low absorption/high transmission) and also reflects from the surface of the liquids, then the result is known as a mixed mode spectrum: partially transmission-like partially specular (refractive-index).

In a method for using the QCL spectroscopy system 100 to remotely record the spectrum from a pool of liquid or a liquid smeared or spilled on a surface, the QCL spectroscopy system 100 is used in a remote stand-off arrangement, to measured spills on a linoleum surface at a distance of about 3 feet. The obtained spectra will compare well with those recorded in the laboratory. The generated absorbance form of the spectra is directly compared to the laboratory reference spectra for characterization and identification. This is a good example where an unknown spill is observed, such as a potential HAZMAT spill, and the material can be safely identified from a distance. This is in contrast to existing FTIR and Raman handheld instruments that require the user to be in a HAZMAT suit and be in extremely close proximity to the hazardous material.

Here also, materials deposited as thick films, designated "infinitely thick" relative to the IR absorption, will yield characteristically distorted specular reflectance spectra. Numerical conversions such as the KK-transform (Kramers-Kroenig Transformation) are applied to reformat the data into an absorption-style of format, by separating the refractive index components from the spectra.

For both residues or thin films and for liquids on surfaces, the spectra obtained by stand-off measurement with the QCL spectroscopy system 100 are reproducible and can be correlated to standard reference spectra when available. The spectra have anticipated "distorted" appearances that are understood and are a function of the nature of the sample and the sample film thickness. These reflection/refractive index effects from the thicker films are reproducible and are equally characteristic of the sample spectrum as the normal transmission spectrum. The chemical agents can be both characterized and identified from the stand-off spectra by building a custom data base that features transmission, mix-mode and specular (refractive index) spectral data. The KK transform is preferably applied to examples where the spectral data is mostly specular rather than mix-mode.

Stand-off measurements are important for a wide range of practical applications, for example; surface quality or contamination measurements for engineering and production applications, security applications, where dangerous materials such as chemical agents and/or explosives might be involved, and for law enforcement, such as for illicit drug detection (both production and usage). Unlike other methods, this can be performed at a reasonable distance, and without contamination of either the surface or the instrument.

Chemical Imaging of Large Surfaces

Figure 14:
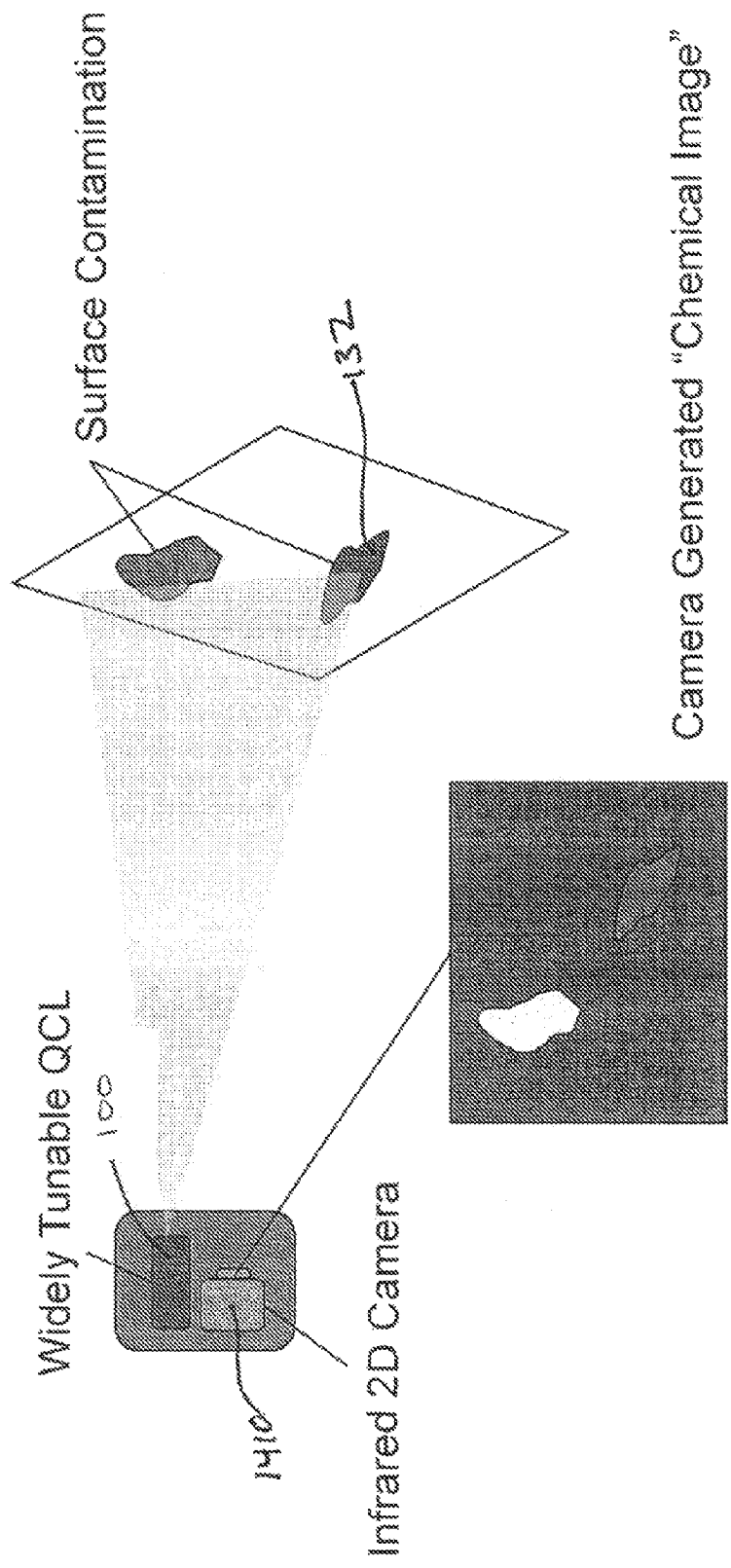
FIG. 14 shows an alternative configuration of the QCL spectroscopy system in which the QCL spectrometer system is used with an IR array to provide a 2D "chemical image" of a surface.

An embodiment of the current invention is drawn to a method for using the a QCL 110 together with an IR array (microbolometer or MCT) to provide a 2D "chemical image" of the surface. This arrangement is illustrated in FIG. 14. It comprises the QCL laser 100 that images a sample 132. An image of the sample 132 is then detected by an infrared camera 1410 that comprises a two dimensional detector array such as a 100 by 100 element microbolometer array. This allows scanning a surface to detect the presence of Explosives, chemical warfare agents (CWAs), toxic industrial chemicals (TICs), and non-traditional agents.

Applications include:
 a. Validating that military or emergency response vehicle has been decontaminated.
 b. Validating that a large area, such as a warehouse, office building, etc. are decontaminated.
 c. Scanning the trunk/door handles or tires of vehicles as they enter parking lots, underground garages, or other areas.
 d. For detection of explosive residues to avoid car bombs at large crowd gathering events.

The QCL laser 110 in combination with the IR array 1410 could be tripod mounted for large surfaces, of a vehicle, for example, or portable for the trunk/door handles.

When used for large Area Scanning, each 1.5'×1.5' section is imaged at 100×100 resolution (4.6 mm spatial resolution) of the bolometer. Surface concentrations of 10 g/m$^2$ or less are preferably detected. When 24" optics are used, the total area to be interrogated is 800 sq. ft. Scanning can be completed in 11 minutes.

Figure 15:
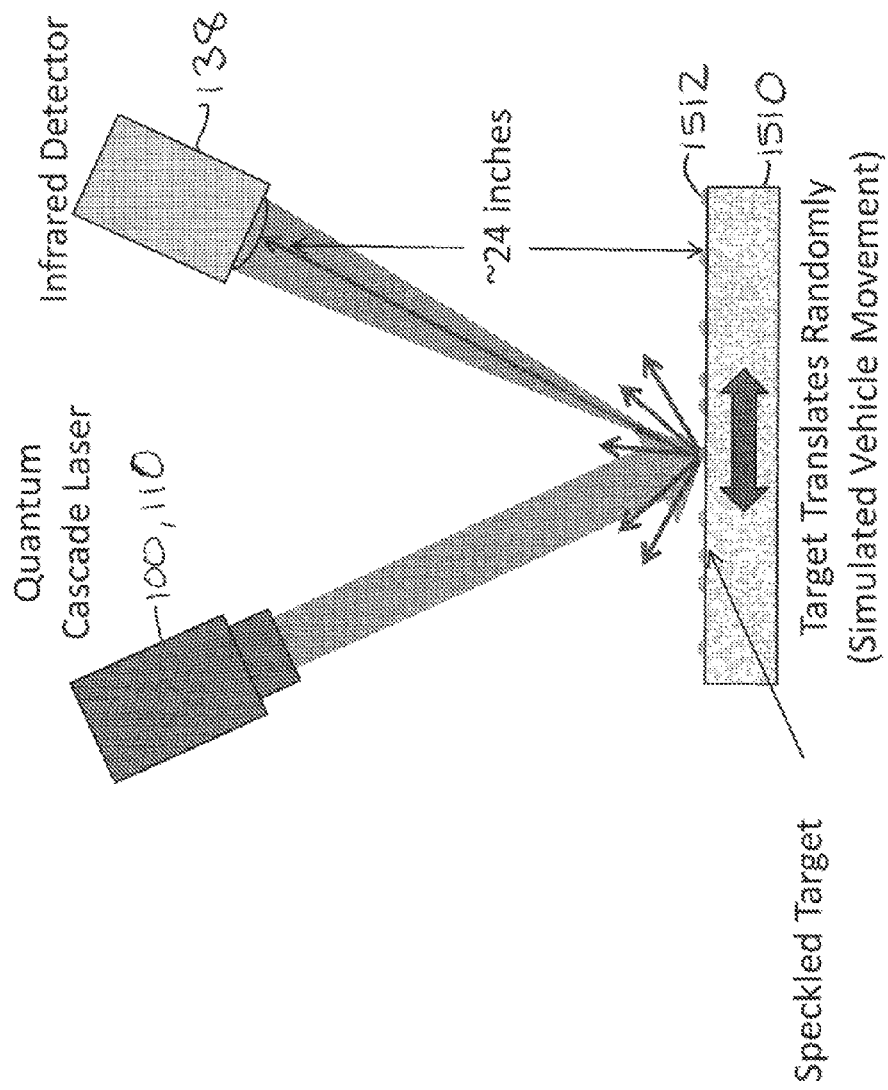
FIG. 15 shows an alternative configuration of the QCL spectroscopy system in which the QCL laser is separated from the detector for detection of scattered contamination.

Smaller, targeted area scanning (e.g. Car Trunk Handle) enables:
 a. Portable equipment
 b. Rapid scanning in seconds
 c. Trace-level concentration detection
 d. Low-cost device Detection of Scattered Contamination on Surfaces One embodiment is drawn to a method and system for detecting scattered contamination patterns on surfaces using the QCL spectroscopy system 100. As shown in FIG. 15, the QCL-based device 100 is mounted under or next to a vehicle and shines the emission from the laser module(s) 110 on the ground or vehicle 1510 for detection of scattered contamination. The detector 138 is separated from the QCL modules 110 to detect the diffuse reflectance spectrum. Such contamination patterns might be typical of a situation when an explosive disperses the chemical threat (e.g. CWAs/TICs/NTAs) over a large area and typically there are droplets 1512 scattered on the surface 1510.

The QCL spectroscopy system 100 scans the surface randomly and collects spectra, which after certain averaging show that a threatening substance is present.

In other embodiments, high speed QCL scanners (such as the Resonant Scanner) would enable such measurements.

In other embodiments, the QCL spectroscopy system 100 is also mounted on robots or unmanned aerial vehicles for similar operation.

Protection of Large Facilities

Figure 16:
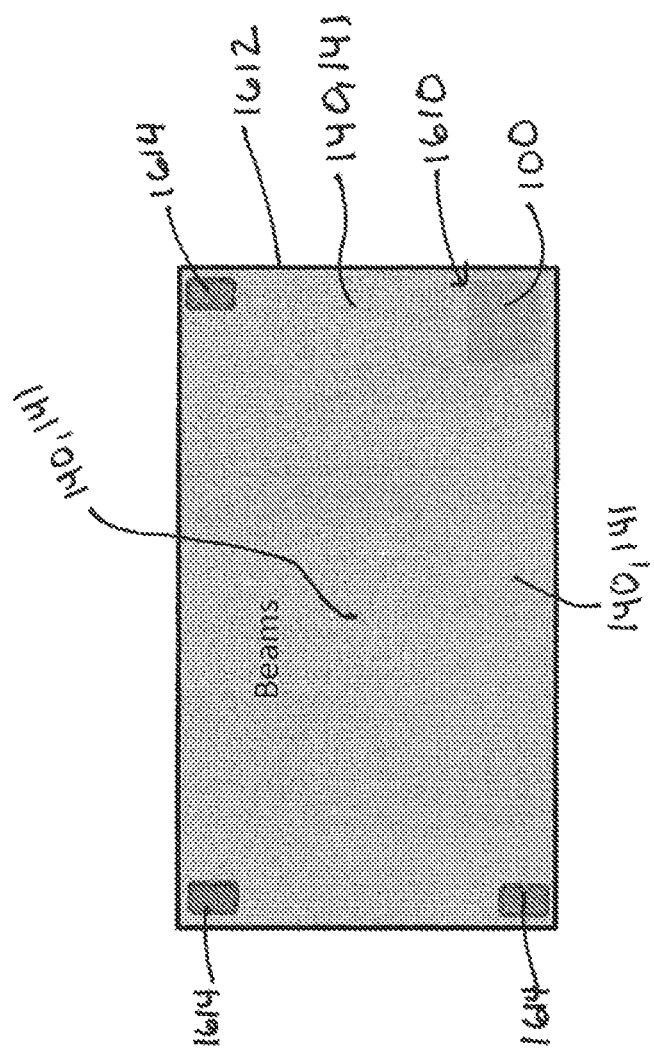
FIG. 16 shows an alternative configuration of the QCL spectroscopy system in which the QCL spectrometer system is placed at a selected location within a room and scans across a long distance by transmitting beams across the room to retroreflectors that generate a return beam.

An embodiment of the current invention is drawn to a system for detecting chemicals at long-range distances using the QCL spectroscopy system 100. The QCL spectroscopy system 100 is placed at a selected location 1610 within a room 1612, such as an airport terminal. The system 100 scans across a long distance by transmitting beams 140 across the room 1612. Properly placed retroreflectors 1614 are used to generate a return beam 141 back to the system cover the area to be protected. This arrangement is illustrated in FIG. 16.

The retroreflectors 1614 provide essentially an "optical path" for detection of any chemical threats, such as gases or vapors from explosives, CWAs, TICs, or NTAs. In one embodiment, multiple retroreflectors 1614 are used, being located in different corners of the room 1612. The beam 140 from the system 100 is either divided into three beams or successively transmitted to each of the retroreflectors 1614, depending on the embodiment.

The eye-safe lasers can be used in areas with large crowds of people, both indoors and outdoors. Fast readings allow for quick detection and immediate warning alerts. 24/7 coverage can be provided with the laser bouncing off the retroreflectors 1614 in a preset timing pattern.

The use of the QCL spectroscopy system 100 in the current arrangement with low-cost, optimally placed retroreflectors 1614 provides real-time large area protection and high sensitivity line of sight detection.

Combined Gas and Standoff Detection in Single Device

An embodiment concerns a system for detecting chemicals at a stand-off distance and detecting gas using the QCL spectroscopy system 100. This system allows users to detect both harmful vapors and surface contaminants with a single device.

The system has a projected gas detection limit: $SF_6$: 8 ppt, Sarin: 70 ppt, Mustard: 237 ppt (5-10 m path).

Advantages of the system include a reduced false alarm rate when compared to IMS (high resolution IR spectroscopy) and the ability to detect a higher number of compounds, including CWAs, NTAs, precursors, impurities, binders, etc. relative to the use of Far IR spectroscopy.

Detection of Chemicals on Shoes

Figure 17:
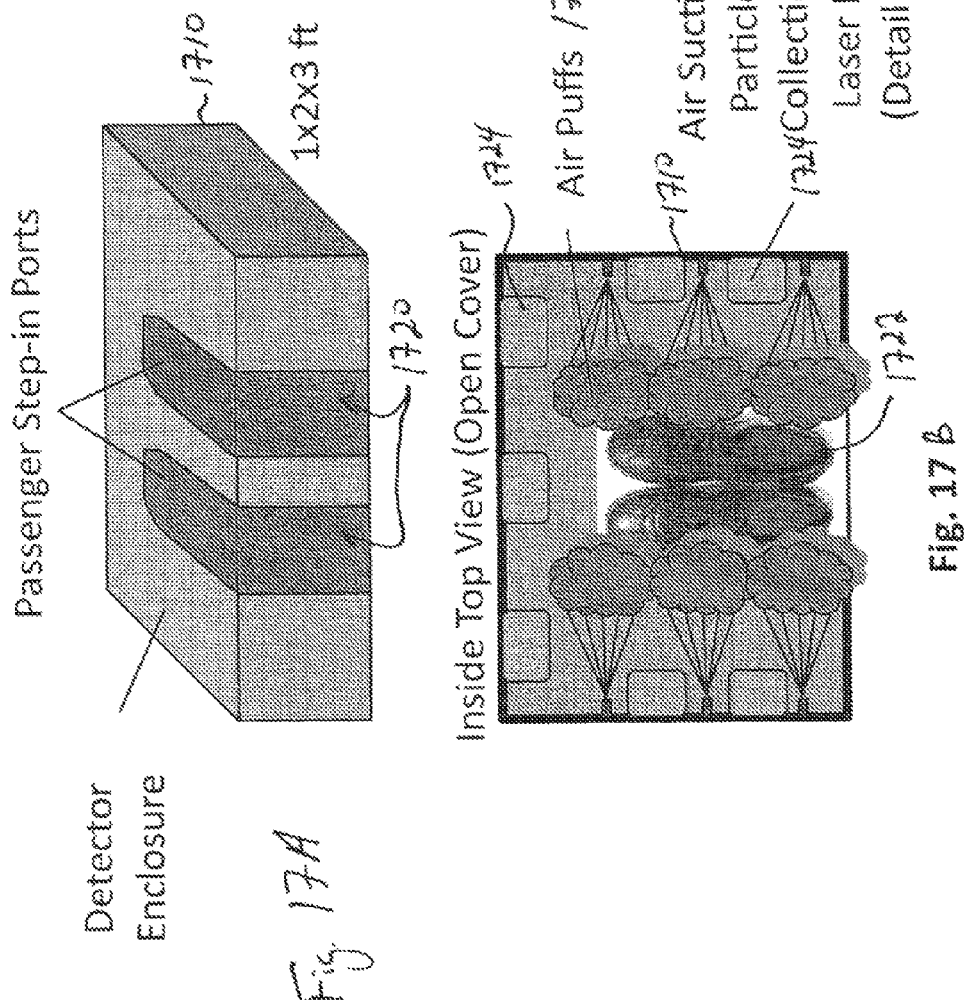
FIGS. 17A and 17B are perspective and top views showing an alternative configuration of the QCL spectroscopy system that detects particles that come off of pedestrians' shoes.

One embodiment is drawn to a system for detecting chemicals on shoes using the QCL spectroscopy system 100. This system is illustrated in FIGS. 17A and 17B. A QCL-based device including the QCL spectroscopy system 100 is used to detect particles that come off of passengers' shoes as they walk through check points, such as airports, events, etc.

In this embodiment, the QCL spectroscopy system 100 is housed in an enclosure 1710. The enclosure 1710 has shoe-sized openings 1720, or step-in ports. When the passenger steps into the step-in ports 1720, their shoes 1722 are puffed with air 1724. A vacuum is then used to suction any released particles onto a silver membrane filter through suction ports 1724. The QCL beam then identifies any chemicals trapped in the filter. Additional embodiments of the invention further comprise magnetometer technology, allowing the identification of explosives in addition to chemicals.

This simple, walk-in concept could greatly contribute to public security by supplementing other, pre-existing safety measures. Scanning is done while other screening is taking place. Sampling time totals only 3-4 seconds and processing time is less than 9 seconds. With a small footprint, at 1×2×3 feet, the detector fits within other systems, such as metal detectors. No additional training of airline or public safety personnel would be required.

Stand-Off Detection of Disturbed Earth Using QCLs

Detection of disturbed soil is of particular importance on the battlefield as it can indicate the emplacement of an improvised explosive device (IED), trip wire or pressure plate. When soil is first disturbed the quartz, found in most soils, is coated with other minerals. As the soil is weathered, the quartz is more exposed, which gives a stronger signature—the Reststrahlen Contrast—particularly in the 8-10 μm (1,250-1,000 wavenumbers) range. So the spectral pattern between disturbed soil and non-disturbed soil is different and recognizable. This effect is particularly important in Afghanistan where much of the soil is sand, with high quartz content, and monochromatic, often making detection of disturbed earth by visual techniques difficult. However, as with most sensor systems, this is not a 100% solution as these spectral differences cannot be discerned during rain, after snow cover or after dust storms.

Spectral analysis research to date has been done with laboratory Fourier Transform Infrared Spectrometers (FTIR), which are slow, require contact with the soil and are not very practical for use in the field. A fast, standoff device is needed to quickly detect the same IR signature changes.

In a method for using the QCL spectroscopy system 100 as a standoff sensor to detect patterns of disturbed earth, the QCL spectroscopy system 100 has a much higher sensitivity than FTIRs thereby enabling standoff detection. The QCL spectroscopy system 100 has been shown to successfully detect the reststrahlen signature.

An additional embodiment of the current invention is the optimization of the portable QCL spectrometer system shown in FIG. 13 for detecting disturbed earth in desert environments. The modified QCL spectroscopy system 100 is lightweight and has low power requirements, enabling it to be carried by dismounted troops or mounted on a variety of vehicles. Furthermore, it preferably includes a rechargeable battery or operates from vehicle power. Power consumption is preferably 30 Watts or less. Operational time on one battery charge preferably ranges from 4-6 hrs at 20% duty cycle. It can tolerate 0-140° F. temperatures, 10-95% humidity, operate at 0-5000 feet above sea level. It is inherently rugged due to its use of solid state components. It can operate either in the daytime or the nighttime. In embodiments, it is further outfitted with GPS, video, RF links and the common sensor interface protocols. It is eye safe. A further embodiment of the current invention is this portable QCL spectroscopy system 100 modified to contain only one laser module. There is great potential for size and complexity reduction because in some examples it is possible to detect the reststrahlen band using only one laser module (versus the three laser modules used in the current QCL spectroscopy system 100 to detect explosives and chemical agents). Using only one module would reduce the cost, size and weight of the laser engine by over 50%.

Figure 18:
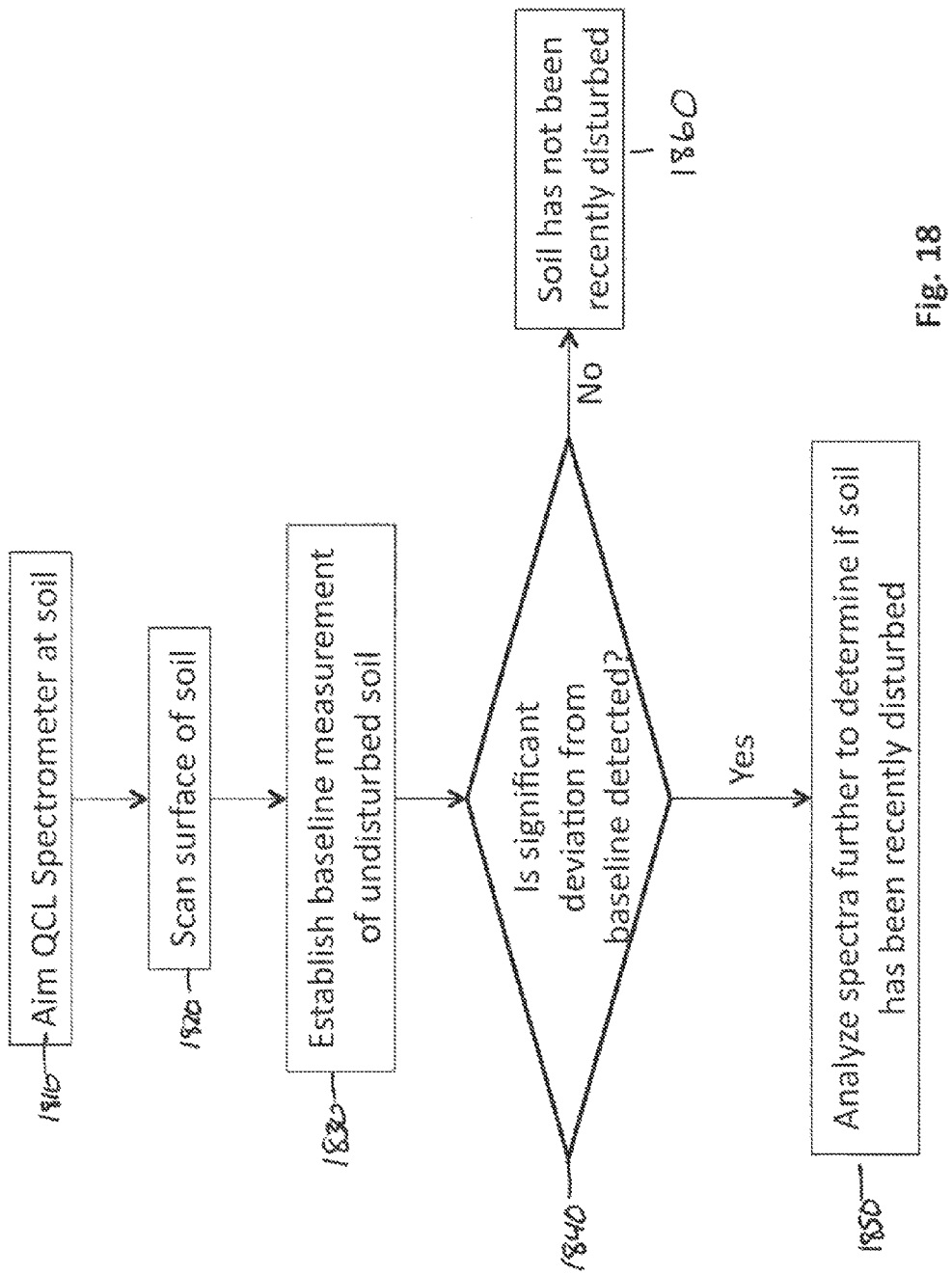
FIG. 18 is a flow diagram illustrating a method for detecting disturbed earth using the QCL spectroscopy system.

FIG. 18 is a flow diagram illustrating the method of detecting disturbed earth using the QCL spectroscopy system 100. In step 1810, the QCL spectroscopy system 100 is aimed at the soil. Most of the time, the QCL spectroscopy system 100 detects the signature of undisturbed soil in step 1820 and uses this data to establish a baseline measurement in step 1830. If no changes are detected from baseline, the spectrometer continues detecting the baseline measurement and notes no changes, as seen in step 1860. When the signature changes, the QCL spectroscopy system 100 automatically detects the change in step 1840 and warrants further investigation as seen in step 1850. Guided by the operator, or potentially with an automatic scanning device, the QCL spectrometer system 100 then interrogates adjacent parcels of soil so as to establish the boundary enclosing the disturbed earth.

The portable QCL spectrometer system used in the current method further includes built in marking devices, such as spray paint, or video feeds that are used to record the location and communicate it back to an operator. GPS or RF modules are also preferably incorporated. At this point other confirmation techniques are also used in some examples to confirm the emplacement of an IED, trip wire or pressure plate and established routines are used to disrupt/disable the IED.

One embodiment of the current invention is the method for detecting disturbed earth using the QCL spectroscopy system 100 mentioned above further comprising a ground penetrating radar (GPR) system such as the VISOR 2500 NIITEK Husky Mounted system to enhance detection performance through a dual sensor system. To cover a large area (e.g. a whole road) the laser is located in a central enclosure in front of the vehicle. A scanner and optical collection system direct the laser beam towards different spots on the ground to increase the interrogation area. The interrogation area is a single 5-10 mm pixel or, for example, a 3×3 sq in area imaged with a 2D multi-pixel array. The array offers a wider ground coverage but the sensitivity of the measurements would be reduced. A line imager could also be used. A further embodiment of the current invention is drawn to method for detecting disturbed earth using the QCL spectroscopy system 100 in combination with NIITEK mentioned above wherein miniaturized versions of NIITEK and the QCL spectroscopy system 100 are integrated into UGVs.

Another method is used for detecting disturbed earth using the QCL spectroscopy system 100 mentioned above, wherein the spectrometer is utilized in a handheld or binocular configuration by soldiers on foot, who are scanning the ground 10-20 ft ahead of them. Dismounted troops often work off road and in narrow pathways, choke points or mountain passes that cannot accommodate sensors mounted on ground or aerial vehicles. In a further aspect of this embodiment, this method detecting disturbed earth using the QCL spectroscopy system 100 in a handheld or binocular configuration is used to search for trip wires. Walking parallel to, but at a safe distance from a road, the soldier finds earth disturbed when trip wires are buried. Special audio or visual warnings instantaneously alarm the soldier as the disturbed area is approached. This sensor is potentially miniaturized so that it is mounted on the helmet of dismounted soldiers, offering convenient "hands-free", real time disturbed earth detection.

A further embodiment is drawn to a method for detecting disturbed earth using the QCL spectroscopy system 100 mentioned above in which the QCL spectrometer 100 is integrated with an interrogation arm. The QCL spectroscopy system 100 is mounted on the IED Interrogation Arm developed by Night Vision and Electronic Sensors Directorate to supplement existing sensor modalities (video and metal detectors).

The method for detecting disturbed earth using the QCL spectroscopy system 100 described above is modified so that the QCL spectrometer 100 is integrated into unmanned aerial vehicles (UAVs). Because of its low weight, the portable QCL spectroscopy system 100 shown in FIG. 13 is mounted on a small payload UAV that hovers only a few meters above the ground. Alternatively, a QCL spectroscopy system 100 with larger collection optics and more powerful lasers, although slightly heavier, could potentially detect disturbed earth from a UAV several meters above the ground.

Figure 19:
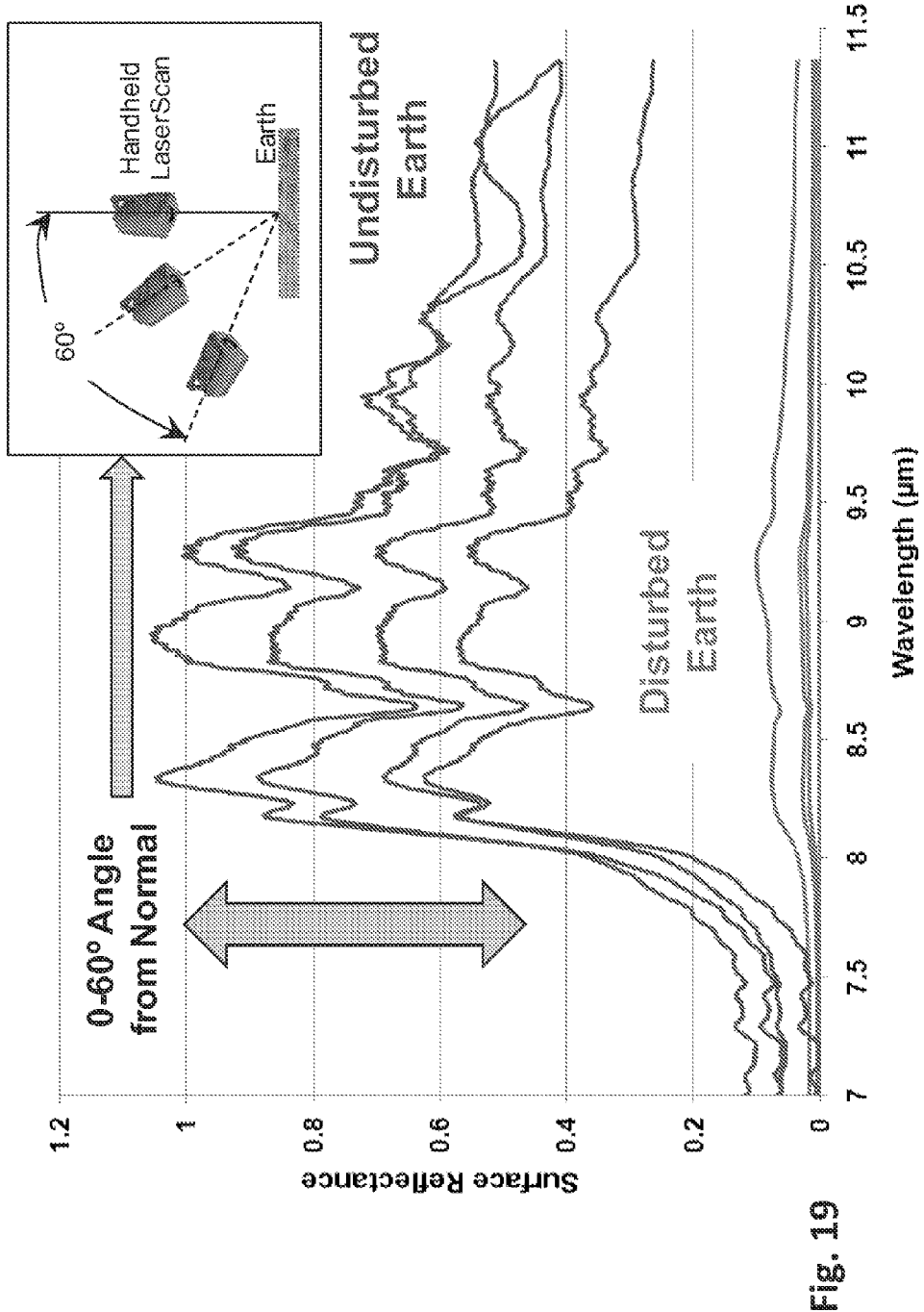
FIG. 19 is a plot of surface reflectance as a function of wavelength generated at varying angles of intersection of the laser with the ground.

FIG. 19 shows data collected using the commercial portable QCL spectroscopy system 100 shown in FIG. 13 on standard soil around the Massachusetts countryside. The curves of disturbed/undisturbed earth deviate from each other in the 8-10 μm range and then approach each other around 7.5 μm. The portable QCL spectroscopy system 100 shown in FIG. 13 was held at approximately 6 inches off the ground and the measurements were acquired in a few seconds. The 6 inch distance was used because the current commercial portable QCL spectrometer unit was designed and optimized for this distance. Other designs would increase the standoff distance. To simulate a "looking ahead" arrangement, under which a dismounted soldier or vehicle are looking ahead of them at a distance, the QCL spectroscopy system 100 was also used to test the effect of angle on the measurements. Assuming the QCL spectroscopy system 100 is held 3-4 ft above the ground and looking ahead at ground 10 ft away, the QCL spectrometer beam will intersect the ground at approximately a 60° angle from normal perpendicular. FIG. 19 shows the results of measurements at angles varying between 0 and 60°, indicating that the reststrahlen effect remains very strong even at steep angles. Using a slightly larger 6" lens and with the sensitivity enhancements, we predict that a handheld QCL spectroscopy system 100 could detect disturbed earth at 10 feet away. As mentioned above if only one laser were used, the device could shrink to flashlight size and ultimately be helmet mounted.

A further embodiment of the method for detecting disturbed earth using the QCL spectroscopy system 100 mentioned above comprises using Differential Spectroscopy (DS) algorithms. The use of DS algorithms is a technique used by spectroscopists to detect "anomalies" in a data stream. DS compares one measurement to the next one over time and identifies changes attributed to a change in the target properties. DS is typically not used with FTIRs because they are too slow and require contact with the sample. The QCL spectroscopy system 100 has been developed as a high speed device and acquires near instantaneous spectral information from the ground. As part of the DS algorithm, algorithmic techniques ranging from Peak Finding and Match Filter methods, to First/Second Derivatives techniques and other more involved mathematical tools are incorporated. These allow the detection of the telltale spectral change in a wide variety of soil types and environmental conditions and to measure changes over time.

When the QCL spectroscopy system 100 is used by dismounted soldiers, special provisions are included. For example, when a soldier is stressed (e.g., under assault) the QCL spectroscopy system 100 might accidentally be pointed at the sky or objects other than the ground (such as a building, another soldier), so the algorithm needs to know when it is seeing ground. To accomplish this low cost MEMS accelerometers and gyroscopes (used in many consumer products) are incorporated to determine whether the QCL spectroscopy system 100 is properly pointed within a preselected cone of, say, 50-70° degrees off normal perpendicular, and appropriately process or ignore the data (or signal the soldier) depending on the reading.

The method for detecting disturbed earth using the QCL spectroscopy system 100 mentioned above further includes using thermal sensors (FLIRs) to detect disturbed earth. A QCL spectroscopy system 100 incorporating a FLIR constitutes a good dual sensor approach.

Figure 20A:
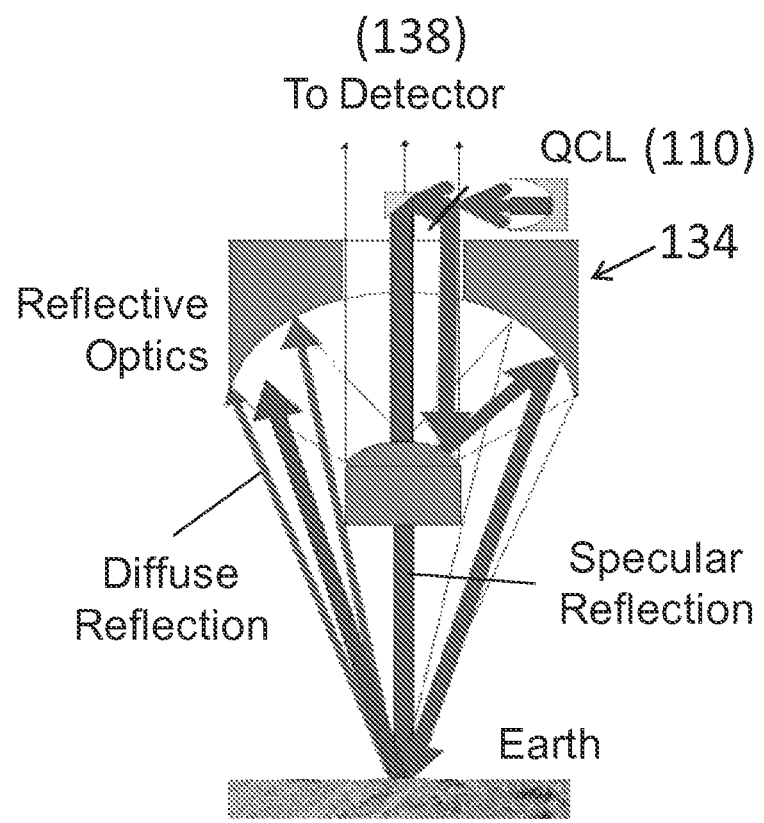
FIG. 20A illustrates a QCL Cassegrain optical system.

A further embodiment of the current invention is drawn to a method for detecting disturbed earth using the QCL spectroscopy system 100 mentioned above in which the QCL spectroscopy system 100 has enlarged collection optics 134. After the laser beam is bounced off the earth, the size of the collection optics determines how many photons are focused on the IR detector 138. More photons enhance sensitivity. FIG. 20A illustrates a QCL Cassegrain optical system. Cassegrain mirrors are lighter than lenses; therefore, collection systems as large as two feet in diameter can be practically developed and deployed.

Figure 20B:
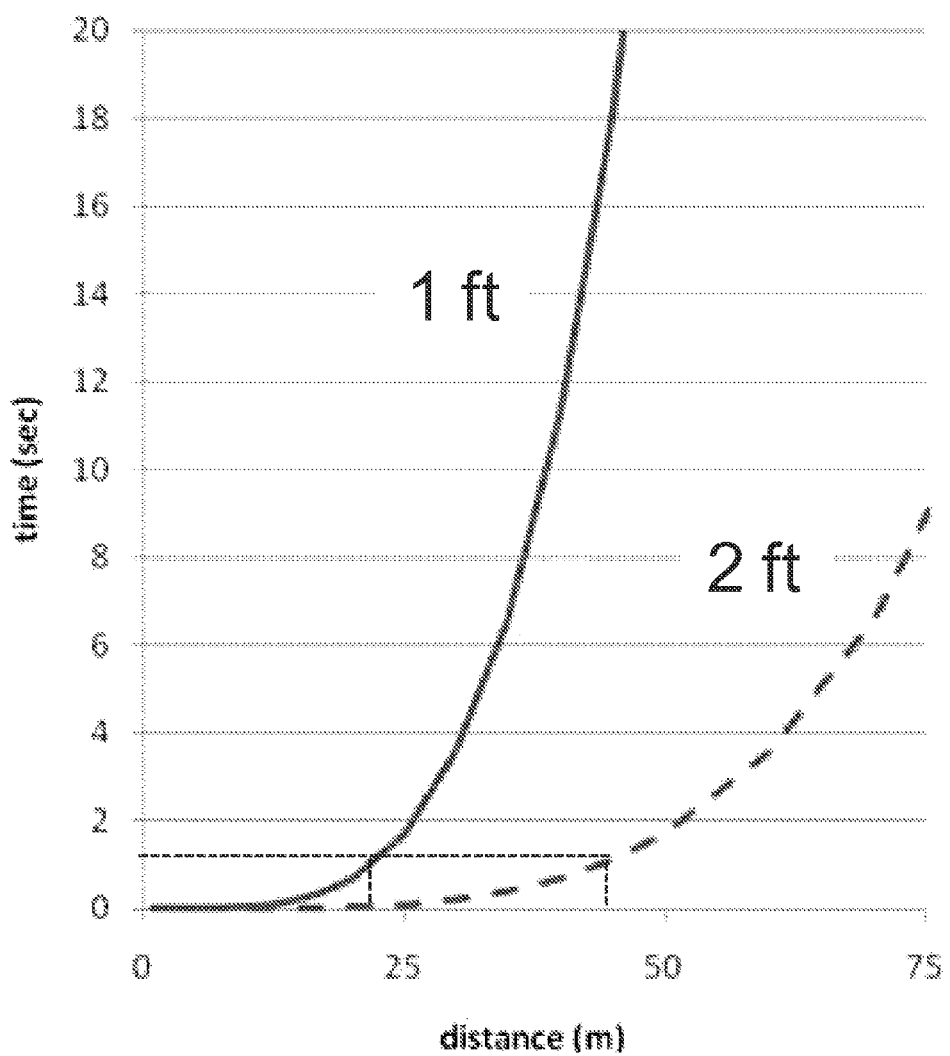
FIG. 20B is a plot of measurement time as a function of standoff distance generated with varying collection optics.

Using extensive data from various backgrounds, substrates, substances, and distances, the performance of the QCL spectroscopy system 100 under various conditions and configurations can be predicted. FIG. 20B shows the effect of larger collection optics on the standoff distance for detection of disturbed earth. Standoff distances of approximately 20 m or 45 m (~65 or 150 ft) can be achieved with, respectively, 1 and 2 foot collection optics, producing a measurement in one second.

A further embodiment of the method for detecting disturbed earth mentioned above includes using a QCL spectroscopy system 100 modified to have an increased duty cycle. The QCL spectroscopy system 100 operates at 200,000 pulses per second, but there is still quite a bit of "silent" time between pulses resulting in a duty cycle of only about 2%. A low duty cycle allows for laser cooling and temperature stabilization between pulses. However, QCL spectrometer systems can be used in which the duty cycle is increased to 10%, i.e. by as high as a factor of 5, which would increase sensitivity by a similar factor.

The method is further modified to include the use of a QCL spectroscopy system 100 with a higher sensitivity detector. The QCL spectroscopy system 100 uses a TE-cooled Mercury Cadmium Telluride (MCT) detector 138, in the current embodiment. However, QCL spectrometer systems can be used with higher sensitivity detectors, such as immersed TE cooled Mercury cadmium telluride (MCT) that works well for disturbed earth detection and would be 10 times more sensitive.

A further embodiment of the method for detecting disturbed earth includes using a QCL spectroscopy system 100 with increased laser power. Higher currents are used to increase the power per laser pulse by a factor of 3-5.

Stand-Off Applications in Pharmaceutical Environments

In addition to the military and public safety applications described above, the QCL spectroscopy system 100 has many uses in the laboratory or pharmaceutical environment. When used in a standoff arrangement, the QCL spectroscopy system 100 is a new and useful tool for both assessing contamination in pharmaceutical environments and for bacterial identification. Both of these applications will be described in further detail below.

Reaction Vessel Contamination Monitoring

The conventional process for monitoring contamination in reaction vessels involves taking several swabs in pre-identified "hot spots" of a 10×10 cm area within a reaction vessel to verify cleanliness. Methanol is used to remove the potential contaminants from the swab and then HPLC or TOC is used to detect contamination. The threshold level of contamination is typically approximately 1 ug/cm2. Although there are some active ingredients that need to be as low as 0.015 ug/cm2, the vast majority are above 0.6 ug/cm2. Perhaps 50% are above 1 ug/cm2.

The Food and Drug Administration (FDA) requires three successful cleaning runs, where the cleanliness of the vessel is verified after each run in order to validate the cleaning methodology. After this validation there is no need to test for cleanliness between switch over, as long as the validated cleaning method is used. The problem is that this is not a very empirical method—how hard or thoroughly did you swab the area. Also, it is time consuming because it takes a several minutes at least to get results. Ideally, a user would like to go to cleaning monitoring after each switch over. Through cleaning monitoring they will be able to clean the vessel until the contaminants are down to acceptable levels, rather than cleaning until they reach the validated standard (which might require overcleaning the vessel and using excessive water and time). There are various other alternative techniques, but they each have problems:

Raman is not sufficiently sensitive in its handheld embodiment.

UV spectroscopy has a hard time working with the surfaces.

One embodiment of the current invention is drawn to a method for detecting contaminants on pharmaceutical surfaces using the QCL spectroscopy system 100. In the preferred embodiment, the QCL spectrometer 100 described previously is used in a standoff arrangement, such as 0.15 to 0.3 meters from the inner wall of the reaction vessel, to analyze the inner reflective surfaces of the reaction vessel. Preferably the device is deployed in a standoff mode or combined with a grazing angle probe coupled to it by a fiber. By taking high sensitivity measurements at a standoff it becomes a practical device for doing contamination monitoring.

Figure 21:
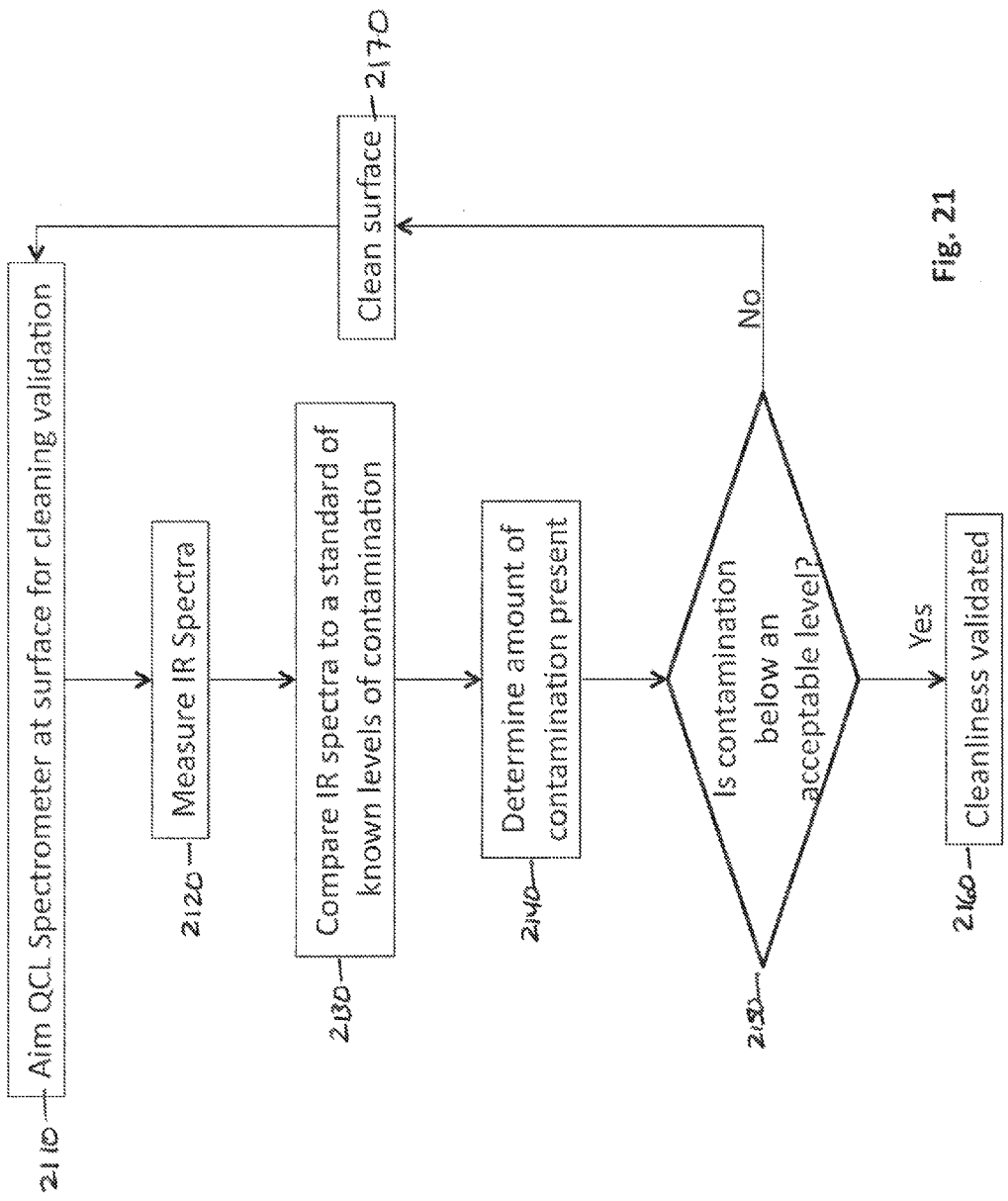
FIG. 21 is a flow diagram illustrating a method for validating surface cleanliness using the QCL spectroscopy system.

FIG. 21 is a flow diagram illustrating the method of detecting contaminants on pharmaceutical surfaces.

In step 2110, the QCL spectroscopy system 100 is positioned towards a pharmaceutical surface at a stand-off distance. The IR spectra are then measured by QCL spectroscopy system 100 in step 2120. The IR spectra are compared to a standard of known levels of contamination in step 2130 and in step 2140 the amount of contamination present is determined. The level of contamination is compared to a previously determined threshold level of acceptable contamination in step 2150. If the contamination is below this level, then the cleanliness is validated in step 2160. If it is not below this level, then the surface must be cleaned further in step 2170 and the cleaning validation must be repeated.

In an alternative embodiment, the spectra of the pharmaceutical surface can be measured using the QCL spectroscopy system 100 fiber optically coupled to the grazing angle probe shown in FIG. 6. The use of fiber optic probes is discussed further below.

QCL-Based Detection of Bacteria

Bacteria that are confined in a vial and given nutrients emit certain characteristic gases based on the type of bacteria in the vial and based on the nutrients they are given. These gases rise into the head space of the vial. Measurements are taken across the vial using the QCL laser based absorption spectroscopy system 100. These measurements have been taken previously with an FTIR, but with a QCL there is more energy per wavelength, which results in faster measurements and measurements with lower detection levels.

Figure 22:
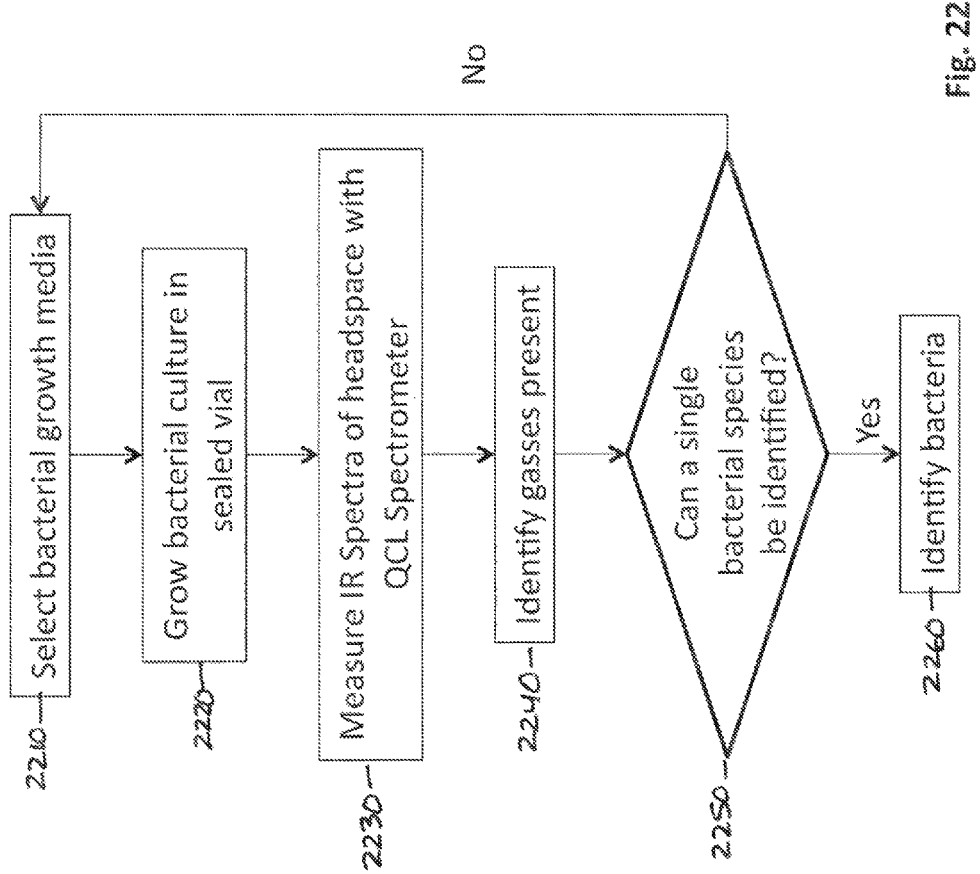
FIG. 22 is a flow diagram illustrating a method for identifying bacterial species using the QCL spectroscopy system.

FIG. 22 is a flow diagram illustrating the method of identifying bacteria using QCL spectroscopy system 100.

In step 2210, an appropriate growth media is selected. Different types of growth media will cause the bacteria to produce different gaseous products. In step 2220, a pure culture of bacteria is grown in the media in a sealed vial, allowing any gasses produced during the growth of the bacteria to accumulate. In step 2230, the IR spectra of the gaseous headspace of the vial are measured using the QCL spectroscopy system 100. In step 2240, the spectral data obtained are used to identify the gasses present. The gaseous composition is then evaluated in step 2250. It is possible that the gasses produced are consistent with the presence of a single type of bacteria, in which case, the bacteria has been identified in step 2260. Alternatively, it is possible that the information gained from the gaseous composition has narrowed the field to a few possible types of bacteria. In this instance, repeating the testing process with a different type of growth media may allow for bacterial identification.

Near-Range Use of the QCL Spectrometer System with Fiber Optic Probes

The use of the QCL spectroscopy system 100 with fiber optic probes for near range or direct observation of targets is a significant improvement over previous technology. In the past, when coupling an IR spectroscopy system to a fiber optic probe, such as an attenuated total reflectance (ATR) probe, FTIR was used. As will be described in more detail below, when using FTIR with an ATR probe, the return signal is very weak requiring the use of a high sensitivity detector. When coupled to a fiber optic probe, the QCL spectroscopy system 100 produces a stronger signal, resulting in higher sensitivity and faster measurements. Described below are several different systems and methods for using the QCL spectroscopy system 100 with fiber optic probes that represent significant improvements over prior FTIR-based technology.

Monitoring of Chemical or Biological Reactions with QCL Spectroscopy System 100

Typically, reaction monitoring is done in the mid-IR with a combination of an FTIR coupled to either a fiber, which is then connected to an ATR probe or a light guide connected to an ATR probe. The light source of an FTIR is a conventional globar, which is a large source that is difficult to couple to a fiber or light guide with high efficiency. Because of this, only a small percentage of the light from the globar is coupled into the fiber or light guide. Therefore, the return signal is very weak, which requires a very sensitive detector, such as a liquid nitrogen cooled detector, in order to detect the return signal. Furthermore, the sensitivity of the FTIR based reaction monitoring is limited by the amount of light that is successfully coupled and then returned to the FTIR's detector.

To compensate for high loss (such as through long lightpipes or small diameter fibers), FTIRs typically use high sensitivity, liquid nitrogen cooled detectors. These detectors are inconvenient because they constantly need to be recharged. In addition, an FTIR is extremely vibration sensitive because at its heart is an interferometer.

In the case of using a QCL spectrometer, the laser is more efficiently coupled into the fiber than the FTIR globar source and the power level per wavelength is also higher. This high coupling efficiency is because of the high spectral radiance of the laser based system relative to an FTIR globar source (six orders of magnitude higher). Therefore, the return signal through the reaction monitoring probe is significantly higher than for an FTIR. This results in higher sensitivity, faster measurements, and not requiring the use of a liquid nitrogen cooled detector.

In the preferred embodiment, a chemical or biological reaction is measured by a QCL spectrometer 100 described previously optically coupled to a reaction vessel in or substrate on which the reaction is taking place in process material. The optical coupling is preferably achieved with optical fiber that extends between the spectrometer and the probe such as an ATR probe. A detector is used to detect the light returning from the process material. A controller determines the spectral response of the process material, which is used to assess the progress of the chemical or biological reaction. Preferably, this spectral response is then used by the controller to control the reaction parameters such as time and temperature and other variables that affect the progress of the reaction.

Figure 23:
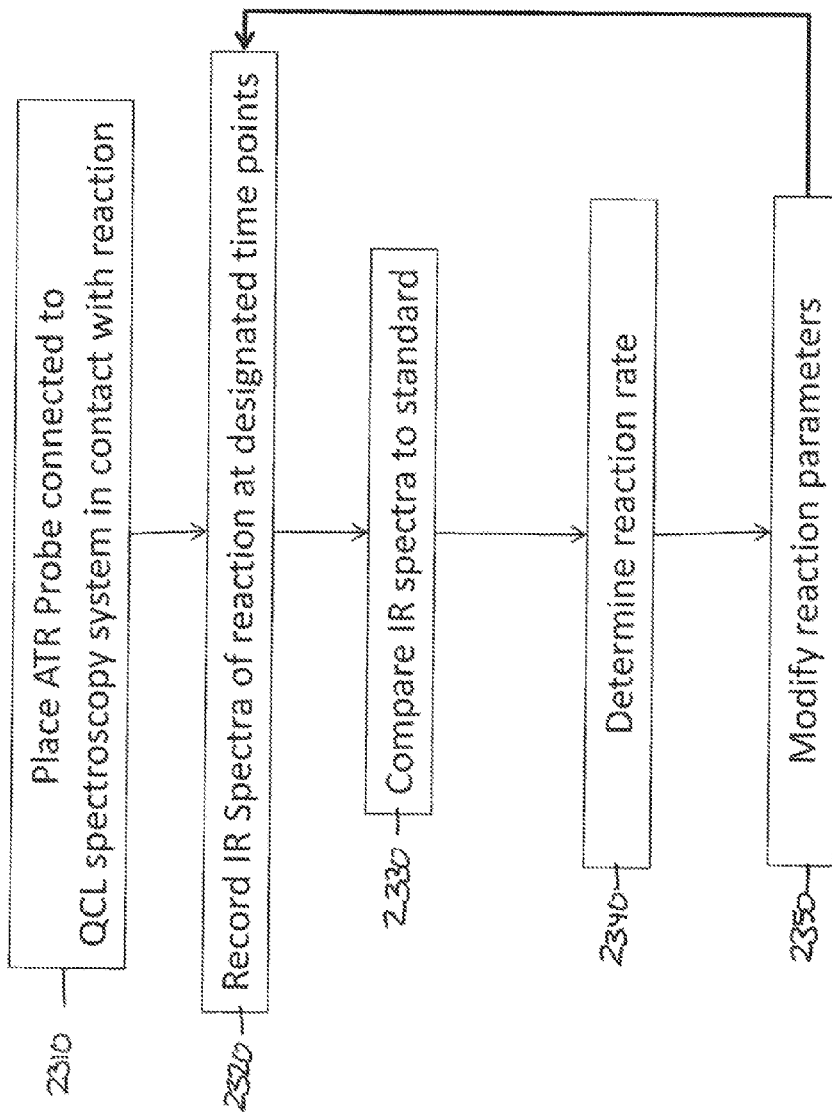
FIG. 23 is a flow diagram illustrating a method for monitoring chemical reactions using the QCL spectroscopy system.

FIG. 23 is a flow diagram illustrating the method of monitoring a chemical or biological reaction with an ATR probe connected to the QCL spectroscopy system 100.

In step 2310, the ATR probe coupled to the QCL spectrometer 100 is placed in contact with a chemical or biological reaction. In step 2320, the IR spectra of the substrate are then recorded by the Quantum Cascade Laser based analysis system 100 at various time points as the reaction proceeds. In step 2330, the spectra obtained are compared to a standard. The rate of the reaction is determined based on this data in step 2340. In step 2350, the reaction parameters may be modified to regulate the rate of the reaction and the reaction rate may be determined.

QCL Spectrometer with ATR Probe for Cancer Detection

The benefits of the QCL attenuated total reflectance (ATR) system versus current cancer detection methodologies are as follows:

1. increased accuracy of detection,
2. operation by relatively low skilled personnel, minimal training required,
3. extremely portable system that can be used in rural areas or in developing countries that do not have access to pathology labs, and
4. a point of care detection system that can be used in clinics and doctor's offices for low cost and more extensive screening of cancer.

Figure 24:
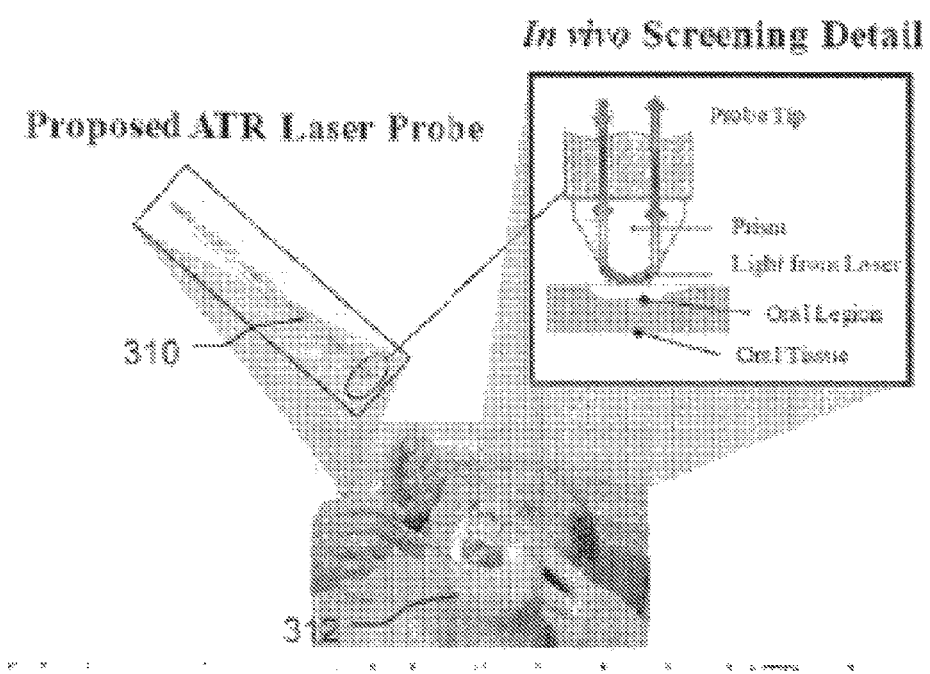
FIG. 24 shows a oral cancer diagnostic application for the QCL spectrometer.

Referring to FIG. 24, infrared technology, with the performance benefits of the QCL, can provide another, different level of diagnostics that is linked to in situ and in vivo measurements. This approach is not micro imaging, but instead is a chemically sensitive probe 310 that is used at the time of an examination and/or an operation on patient 312 to provide the examiner with an instant diagnosis of suspect tissue as shown in FIG. 24. One issue has been the presence of water and/or mucous on the surface of the tissue. ATR probes can be used for the examination of materials in an aquatic environment.

The QCL spectrometer 100 that was mentioned earlier is modified for use with the ATR approach. The benefits offered are similar to those cited earlier, i.e. performance, size and cost, but with the added capability to provide in vivo measurements. The ability to combine the optical throughput characteristics of the QCL system with infrared optical fibers opens up the possibility to provide the examiner with a point-of-care, in vivo, diagnostic tool. For example, this tool is used, in one implementation, by hygienists to look for potential mouth cancers during routine checkups, as shown in the figure. In addition it can be incorporated into colonoscopy probes to detect flat cancerous areas in the colon that are often difficult to detect using conventional visual techniques. Another application is during cancer surgery to determine whether all the cancerous cells have been removed.

In the preferred embodiment, the QCL module 100 is combined with specially designed fiber optic probes into a portable and easy-to-use ATR cancer detection system.

The system provides a clinically-usable diagnostic infrared probe spectrometer system that reliably discriminates between cancerous and non-cancerous lesions in biopsied and fixed tissue examined in vitro or in vivo as shown.

Figure 25:
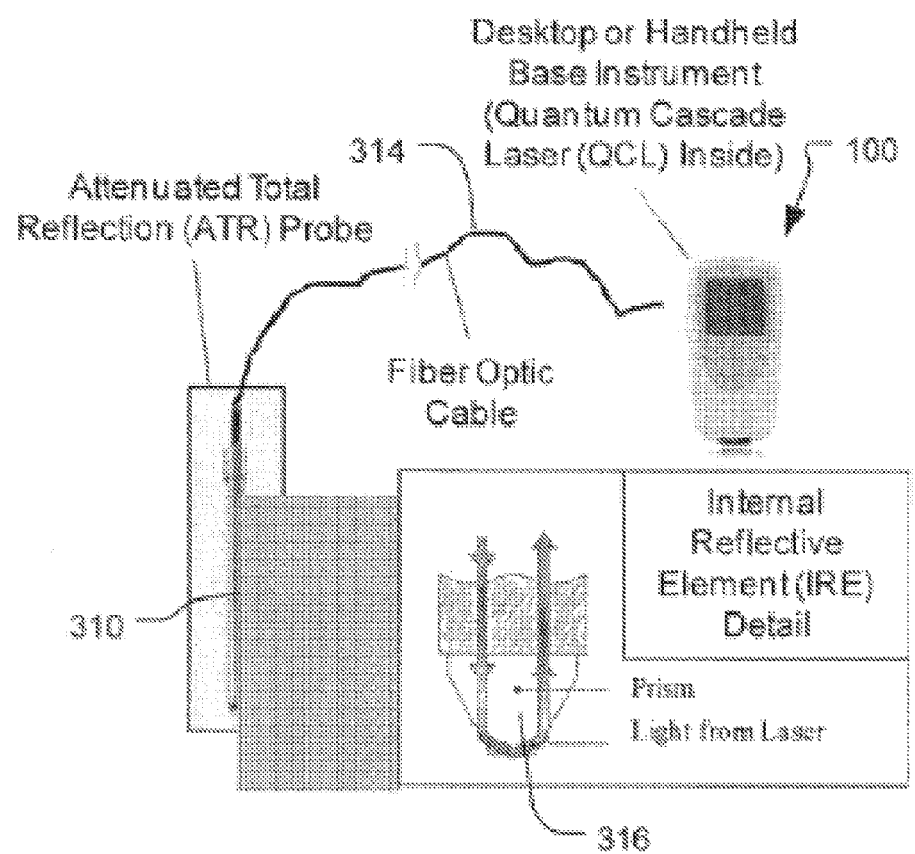
FIG. 25 shows a oral cancer diagnostic QCL analysis system.

FIG. 25 shows Attenuated Total Reflection (ATR) probe 310 and the associated Quantum Cascade Laser (QCL) based analysis system 100.

ATR requires the specially designed optic probe 310 to be made from a high index of refraction optical material. This sampling technique has been applied in infrared spectroscopy for many years. Its use for medical applications began in the 1970s for the study of skin cancer. Since that time it has been used for both the study of normal, healthy skin tissue and also diseased tissue. ATR probes have demonstrated success in examining cancerous tissue that is at or near the surface of the body. The oral cavity is one such area; the cervix and colon are others. Work has already been reported on in situ diagnostics for colorectal cancer patients using an ATR probe. Traditionally, most studies have used an ATR probe on FTIR instrumentation which narrow range limits its applicability. QCLs address this limitation.

In a preferred embodiment, an ATR probe coupled, via optical-fiber umbilical 314, with a widely tunable QCL spectrometer 100, as described previously, covering the spectral range 6 µm to 12 µm, which is the same range typically used with FTIR/ATR systems. This measurement range covers the essential spectral area for infrared cancer studies. Importantly, the QCL spectrometer 100 provides two orders of magnitude greater sensitivity versus an FTIR.

An ATR system includes an Internal Reflective Element (IRE) 316 that is used to probe the tissue, fiber optics 314 transmit IR signals to and from the IRE, and a spectrometer 100 to synthesize the IR signals into a spectra for analysis.

Figure 26:
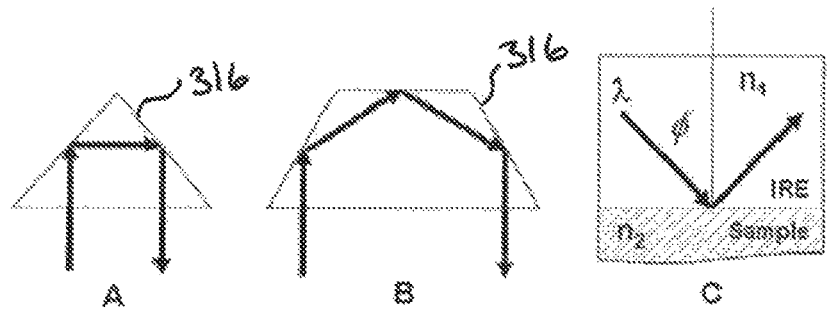
FIG. 26 shows common ATR Configurations.

FIG. 26 shows common ATR Configurations: A. triangular prism 316, B. trapezoidal prism 316 and C. ATR geometric principle.

In order to maximize the sensitivity and utility of the ATR, the IRE is optimized specifically for oral cavity spectral data collection. Both the shape and the material composition of the IRE affect its performance. Materials vary in their refractive index (higher is better), their useful spectral range, their reactions with water and other chemicals and their visible transparency. In order to obtain the ideal internal reflectance within a high index material it is necessary to optimize the device with respect to certain important parameters—namely internal angle of reflectance ($\phi$), the index of refraction of the IRE material (n1), and the wavelength range ($\lambda$) used for the measurement. Also important is the index of refraction of the sample (tissue) (n2).

The goal is to optimize the angle $\phi$, which is affected by the shape as well as n1 and n2. Fifteen different candidate IRE materials have been examined for this application with the best two candidates being diamond and coated silver bromide.

Also important is Dp (depth of penetration), which is the pathlength or the effective thickness of sample that is interrogated. This varies based on the magnitude of φ and n1 for the measurement range. In oral cancer applications a shallow penetration (about 1-5 μm) is preferred so that the IR signal penetrates only the surface tissue layer, where the cancer would reside, and does not pick up deeper tissue that could complicate or interfere with the surface IR signal. Depth of penetration is very relevant to probe both the surface and sub-surface of the epithelial layer, thereby increasing the sensitivity of the measurement. In addition, extending the optical interaction below the surface helps to further reduce spectral interference from water in the saliva.

Figure 27:
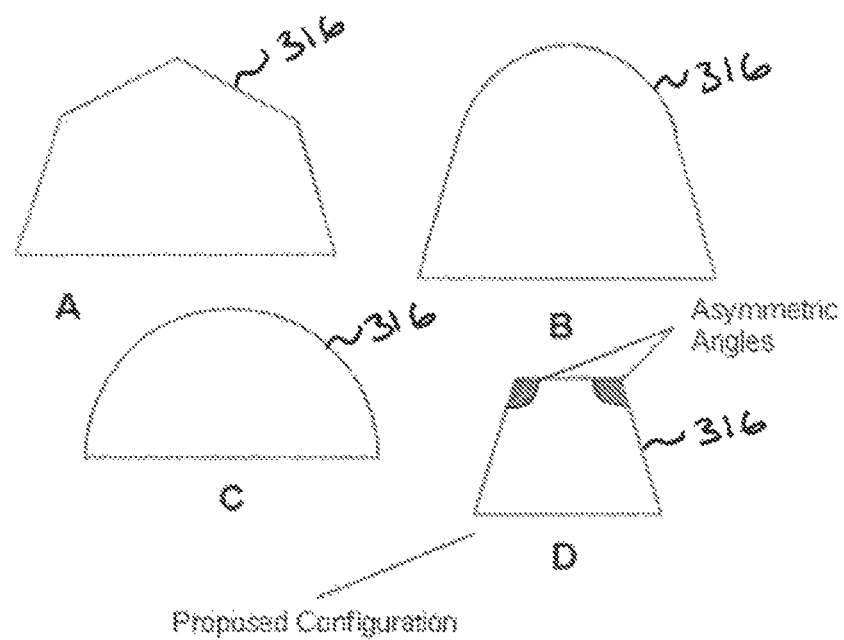
FIG. 27 shows alternative IRE geometries.

FIG. 27 shows alternative IRE geometries for the prism 316. Geometry D is preferred for the oral cancer application, where the top surface is targeted for sample interfacing. The key feature of Geometry D is that the angles provide an asymmetric beam path where there are two different surface angles. This asymmetric design allows the light to enter the IRE closer to the critical angle (i.e. beyond the critical angle light does not reflect from the tip back into the return fiber) and hence be able to penetrate deeper (closer to 5 μm) into the tissue. For comparison, geometry B offers a symmetric angular operation and the depth of penetration is predetermined and more shallow. In difference, under Geometry D the reflection at the top surface is controlled by the angles on the sides and the overall diameter of the top surface, allowing for great flexibility and options.

There are at least three properties/parameters that influence the choice of fiber material for umbilical 314 shown in FIG. 25: spectral transmission range, attenuation (a function of distance/fiber length) and fiber flexibility. Currently, there are three commonly used types of fiber materials for the 6 μm to 12 μm spectral region: chalcogenide glass, silver bromide-chloride (mixed halide) and hollow core fibers. The hollow core fibers have a good transmission and spectral range but are not very flexible and have a limited bend radius, which limits their usefulness when trying to manipulate the probe within the mouth. The best match at this time is the mixed silver halide material. It has the flexibility needed for a probe for use in the mouth although it will need to be properly packaged to ensure that the fiber is not excessively stressed.

The key for the ATR application is to correctly interface the optical fibers 314 to the IRE prism 316 to maximize light throughput. Importantly, the QCL spectrometer 100, which produces a collimated 2 to 4 mm beam diameter, is better matched to the fiber than an FTIR. This feature along with the inherent high power of the QCL provides a signal to noise ratio (SNR) of 10,000:1 compared to reported SNR values between 30 and 150 for similar measurements, using FTIR systems.

Figure 28:
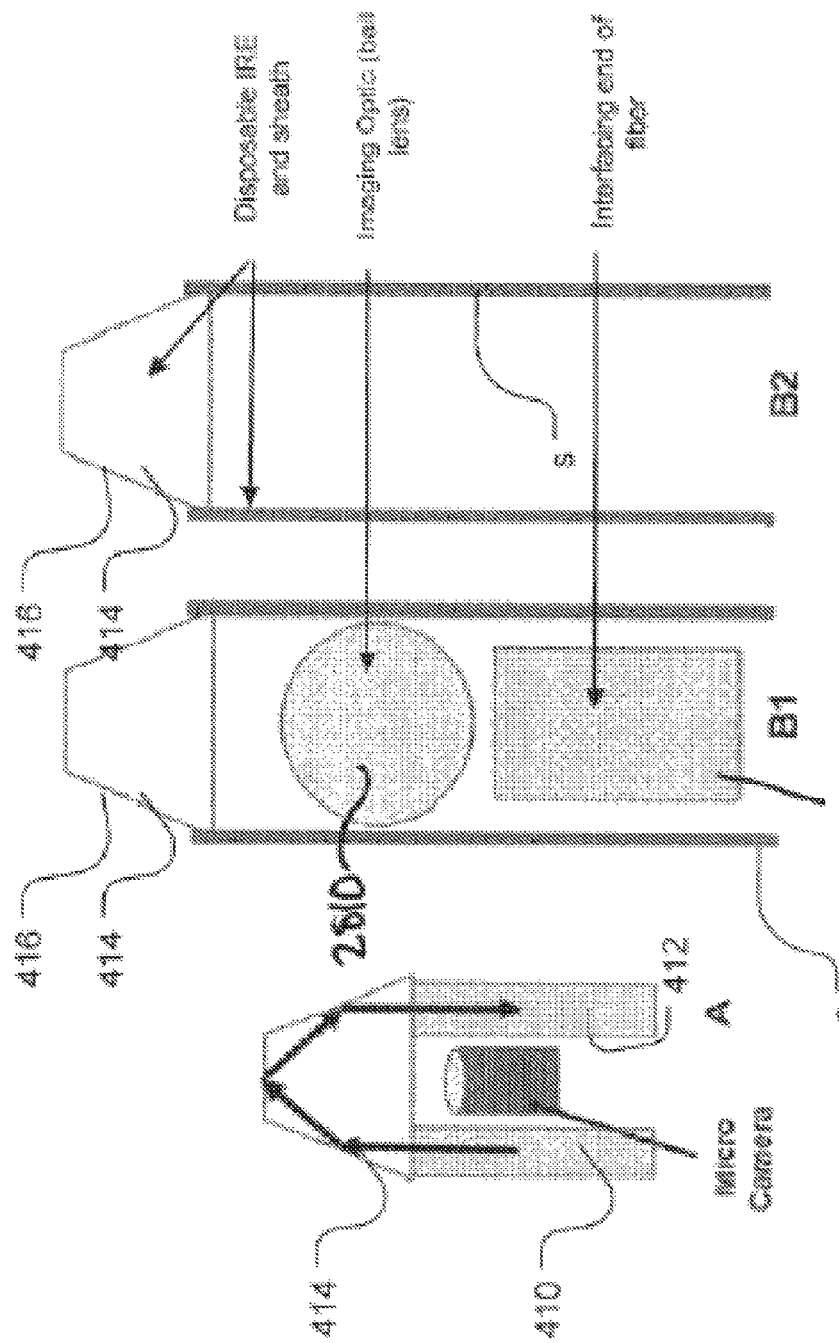
FIG. 28 shows three embodiments of the ATR probe tip.

FIGS. 28A-28C show three embodiments of the ATR probe tip. FIG. 28A uses a two fiber system. See fibers 410, 412, with an integrated micro video camera to enable the point of measurement (the lesion) to be viewed by the examiner; visible light is provided by a third fiber, above the plane of the paper, not illustrated. The camera optics and dual IR fiber adds width to the construction. In this case the reusable probe is designed to be able to be sterilized. It uses, preferably, a diamond IRE tip 414 in a stainless steel housing, not shown. An estimated overall width for such a construction is approximately 5 mm diameter although the effective measurement area on the tissue could be less than 1 mm.

FIGS. 28B and 28C show other embodiments using a disposable tip, which may be preferred in certain clinical settings. FIG. 28B shows the complete assembly with the fiber 314 and imaging optics 2810, and FIG. 28C indicates the disposable components including the sheath s and the IRE prism tip 416. A narrow diameter inner optical assembly is surrounded by an outer jacket or sheath s that is disposable and includes a disposable IRE 414. The sheath is preferably constructed of a suitable rigid molded plastic, such as PEEK (polyketone). To keep costs low, the IRE 414 is molded out of silver bromide. Silver bromide has the ideal optical properties for an IRE vis-à-vis spectral range and index of refraction. Although silver bromide is insoluble in water, it is potentially vulnerable to attack by salts and compounds dissolved in saliva. Therefore, this IRE 414 is coated with a sub-micron thickness of Parylene. This ultra thin coating 416 provides excellent surface inertness while not interfering with the optical properties of the IRE.

Figure 29:
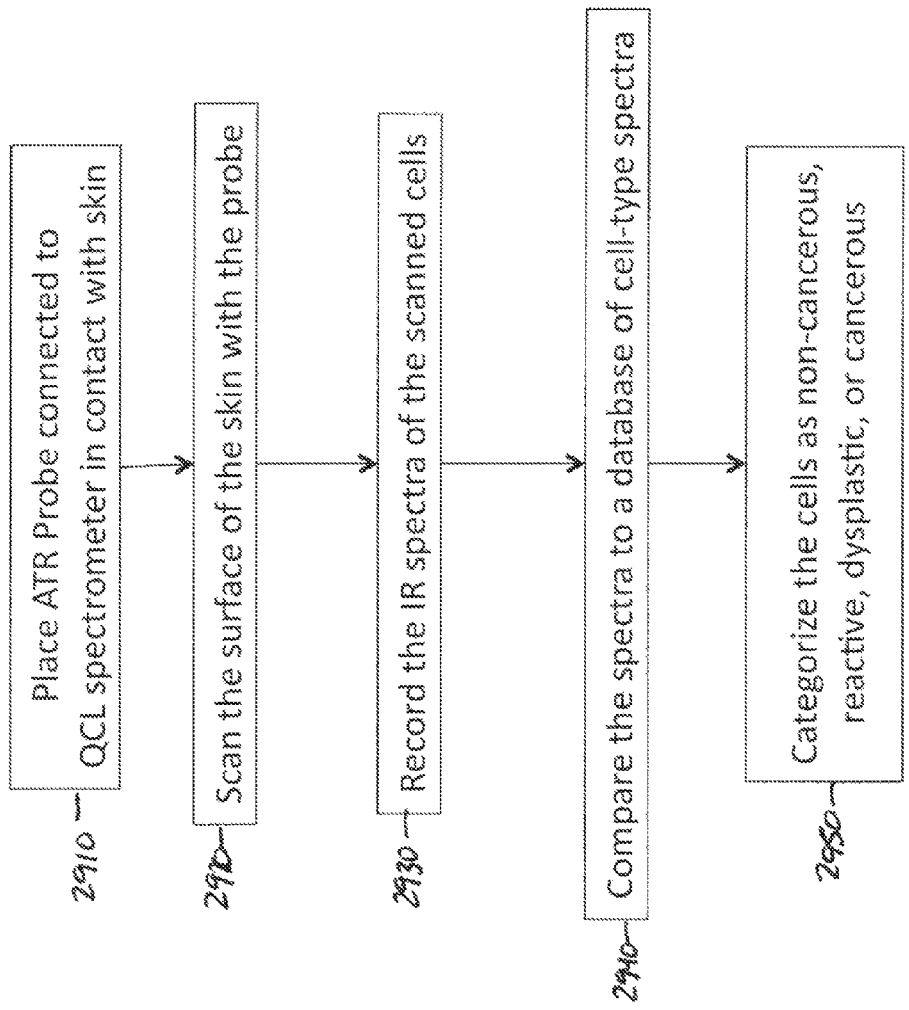
FIG. 29 is a flow diagram illustrating a method for identifying cancerous cells using the QCL spectroscopy system.

One embodiment is used for detecting cancerous cells using the ATR probe coupled to the QCL spectrometer 100. FIG. 29 is a flow diagram illustrating this method.

In step 2910, the ATR probe 310 coupled to the QCL spectrometer 100 is placed in contact with the skin of a patient. The surface of the skin is then scanned with probe 310 in step 2920. In step 2930, the IR spectra of the skin are recorded by the Quantum Cascade Laser based analysis system 100. In step 2940, the spectra are then compared to a database of spectral data of known cell types. Based on this comparison, the cells examined are categorized as non-cancerous, reactive, dysplastic, or cancerous in step 2950.

In the preferred embodiment, the spectrometer 100 acquires spectra quickly, in less than a few milliseconds. This provides an opportunity to obtain both spatial resolution and temporal resolution of the tissue surface. If a small contact area such as 1 mm is moved across the surface under investigation it is possible to obtain differential spectral data with as little as a 10 μm movement (1% of contact area). By providing spectra for just this narrow spatial area (which would look like a new moon sliver), the detection accuracy is potentially increased.

The system is used to evaluate of suspicious lesions to important locations in the oral cavity, namely (1) Tongue, (2) Lip, (3) Floor of mouth, and (4) Other (buccal mucosa, upper and lower alveolar ridge/gingiva, and hard palate). The "Other" category is grouped because it constitutes less than 10% of all oral cancer cases and previous analyses has suggested that these areas so grouped are spectroscopically similar whereas the first three are a bit more spectroscopically distinct.

Detection of Thermal Damage to Composites

The resin of composite materials when exposed to high levels of heat (above 375 degrees F.) becomes damaged and the structural integrity of the material is compromised. The level of damage is related to the temperature that the material is exposed to. The QCL spectroscopy system 100 is used to detect composite damage both in a standoff arrangement and with a fiber optic probe to detect damage within drill holes.

Currently, handheld FTIRs are being used to detect this thermal damage. There is a correlation between the absorption of the material in the Mid-IR, and its level of damage. Specular reflectance is used to measure most thermal damage situations (except heavily abraded graphite fiber composites where diffuse reflectance is used). The bands that change with thermal exposure are generally between 2000 and 700 cm-1 and usually limited to between 1800 and 1000 cm-1.

The problem with using handheld FTIRs is that it is necessary to be in very close contact with the composite material, the measurement takes about 1.5 minutes/sample because of the limited amount of light that is returned to the FTIR, and the spot that is measured is very small.

An embodiment concerns a method for detecting composite damage at a stand-off distance using the QCL spectrometer system. Utilizing a QCL absorption spectroscopy system 100, it is possible to make these measurements at a standoff. The amount of light that hits the sample is significantly higher (on a per wavelength basis) than with an FTIR, which allows for significantly faster measurements. Finally, the effective spot size that is used with a QCL system is significantly larger than with an FTIR system, expanding the effective area that is tested.

The QCL absorption spectroscopy system 100 is able to detect thermal damage in composites from a standoff distance between 6 inches and 2 feet. In one example, the QCL absorption spectroscopy system 100 uses infrared laser absorption spectroscopy across a wavelength range of 1000 to 1600 cm-1 (or 6-10 μm) to detect differences in the spectra collected from damaged and healthy composite surfaces. These differences are typically correlated to thermal damage using software data processing algorithms.

The advantages with standoff, faster measurements, and larger inspection areas is that a device with these characteristics is much more practical for field applications, where very rapidly scanning areas of composite damage are key.

Figure 30:
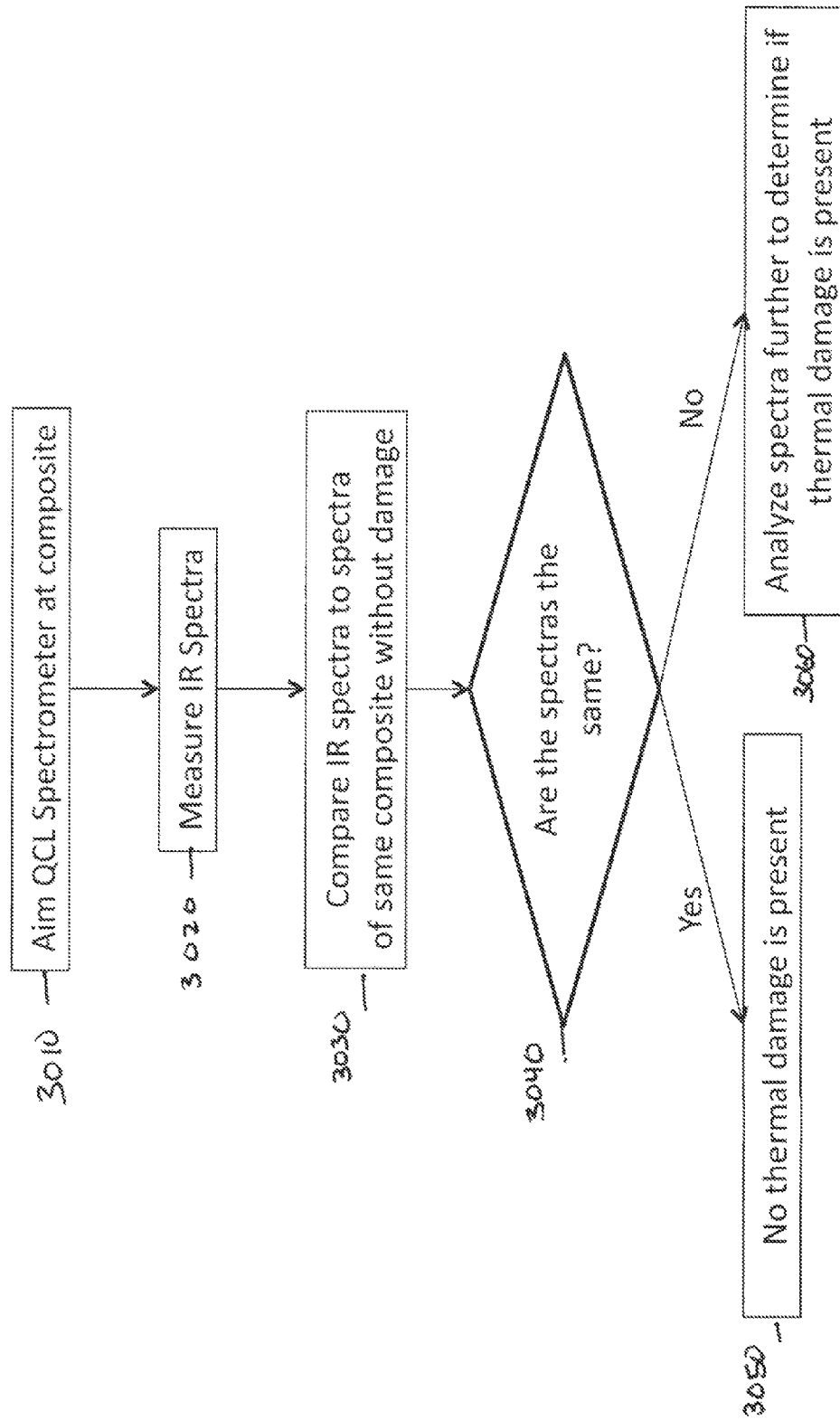
FIG. 30 is a flow diagram illustrating a method for identifying thermal damage to composites using the QCL spectroscopy system.

FIG. 30 is a flow diagram illustrating the method of detecting composite damage at a stand-off distance using the QCL spectroscopy system 100.

In step 3010, QCL spectroscopy system 100 is aimed at a composite surface to be tested. The IR spectra are the measured in step 3020. In step 3030 the spectra are compared to known spectra of the same composite lacking thermal damage. A determination is made as to whether the spectra are significantly different in step 3040. If they are not, then it is determined that no thermal damage is present, as seen in step 3050. If they are significantly different, then the spectra is further analyzed in step 3060 to determine if thermal damage is present and the extent of thermal damage.

Detecting Thermal Damage in Composite Drill Holes

A more specific application of the QCL absorption spectroscopy system 100 in detecting thermal damage in composite materials is the use of the system with a fiber optic probe to detect potential thermal damage to drill holes in composite materials.

This technique detects the thermal damage inside the drill holes. A custom fiber optic probe is inserted into the drill hole, illuminates the sides of the hole, and couples the reflected light back into the system 100.

It is important to detect thermal damage in drill holes. If the drill bit overheats, the section is usually cored out and a larger bolt is used, without verifying whether there was damage.

There are nondestructive testing techniques that are being explored for this application, such as ultrasound. However, the problem is that although these other techniques can be used to detect structural damage, such as delamination, they cannot detect polymer degradation that has a chemical rather than a physical signature.

FTIR has proven effective in detecting some cases of thermal damage to composites. However, it is not possible to couple enough light from an FTIR into the drill hole, to be able to get a signature that can be used for analysis. This is because the source of an FTIR is incoherent and large (e.g. globar) and, hence, it cannot efficiently be coupled into a fiber probe.

In contrast, in the QCL absorption spectroscopy system 100, the source is a Quantum Cascade Laser (QCL), which is a very bright (high spectral radiance) source, which means that it can be coupled with very high efficiency into a hollow silver halide fiber, for example.

The sizes of the drill holes are between about ½ inch to ³⁄₁₆ of an inch. The depth of the holes in composite are ¼ inch to ¾ inch. However, because of titanium above or below the hole, the probe needs to penetrate through a hole that can be between 1 to 1¼ inches in depth. The key issue is making a fiber probe that will be small enough to enter into the holes and illuminate the composite material and then couple that light back into the fiber.

Figure 31:
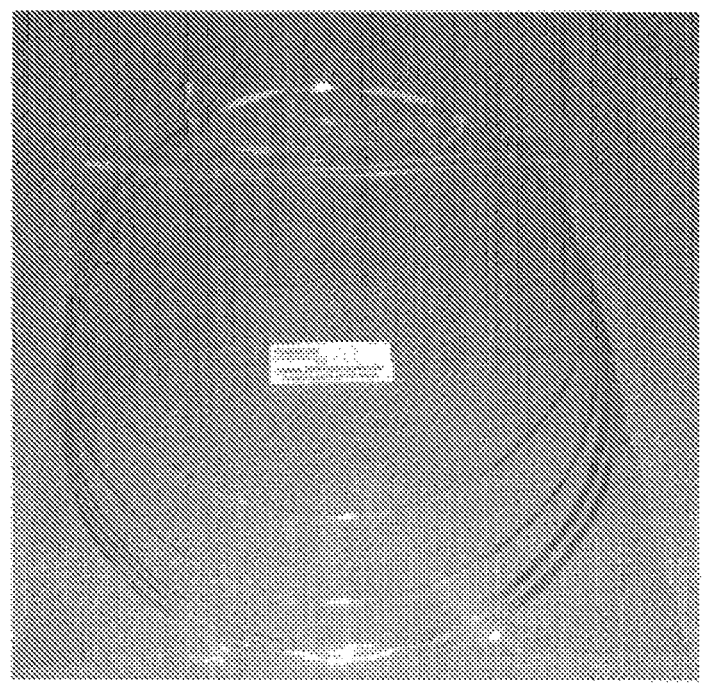
FIGS. 31 and 32 show examples of hollow fibers that are used with the QCL spectrometer system.
Figure 32:
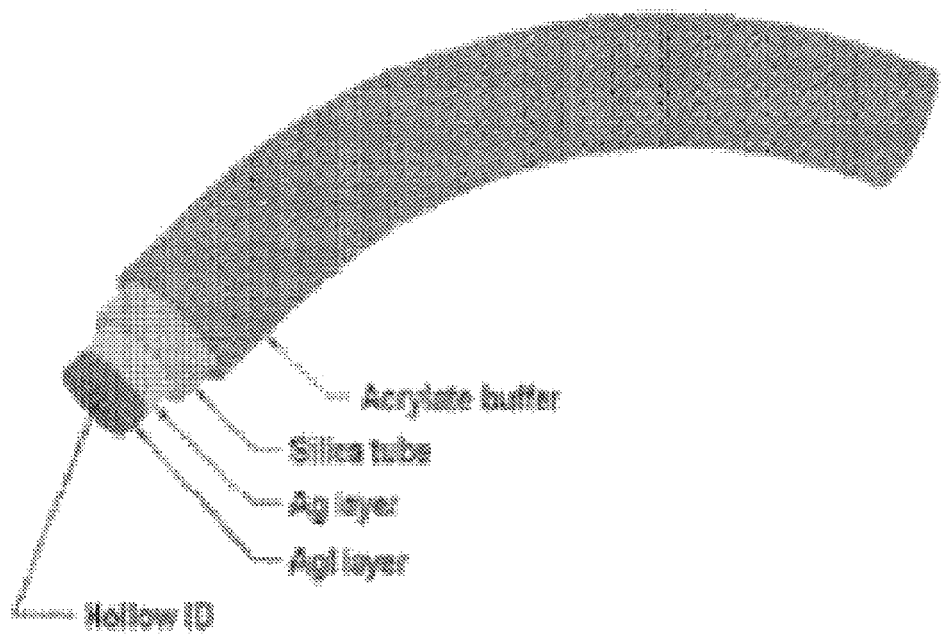
Figure 33:
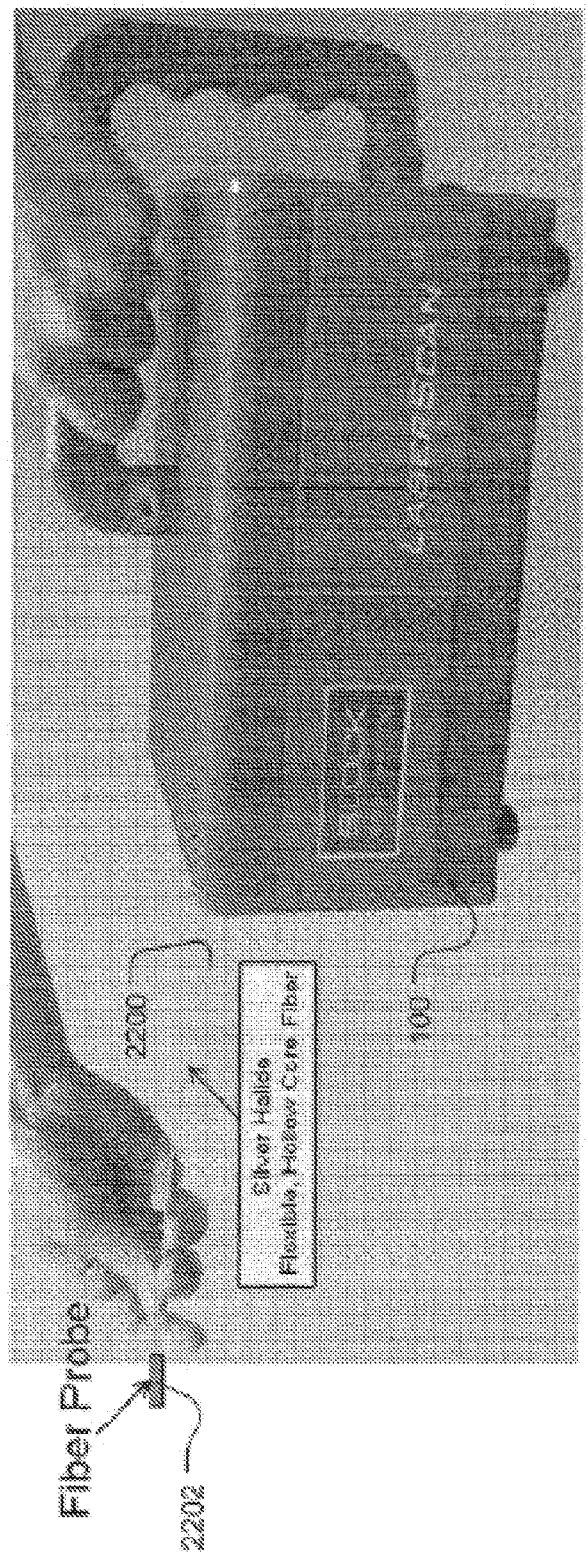
FIG. 33 shows the coupling of the fiber probe to the spectrometer system.

In one implementation, a fiber link to a probe is silver halide or silica hollow core fiber (see FIGS. 31 and 32). The system will be directly coupled to the fiber 2200 which ends in a probe 2202 (FIG. 33).

Figure 37:
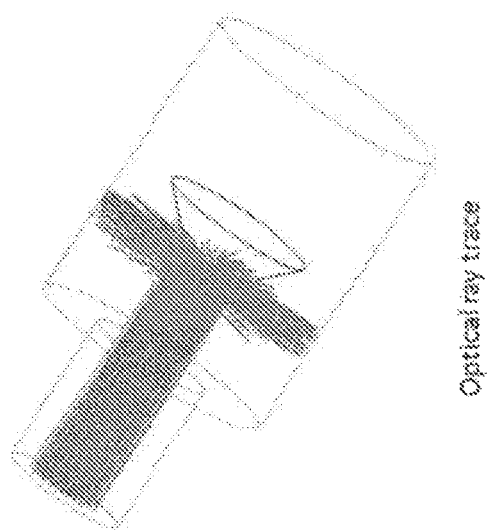

There are various potential geometries for the probe 2202. FIGS. 34-37 show some potential examples. Each of these probes 2202 couple light received from the QCL absorption spectroscopy system 100 to the side walls of the drill hole via a turning mirror, prism or conical reflector (axicon). FIG. 37 is ray trace for the axicon implementation. A microlens 2204 improves coupling between the fiber endface and the turning element. In some examples, returning light from the hole side walls is returned to the spectrometer 100 via the same fiber 2200. In other examples light back to the spectrometer is carried in a second fiber.

FTIR Microscope Using QCL Spectrometer

In a conventional FTIR microscopy, the FTIR spectroscopy system includes a relatively large, broadband, mid-IR source, the emission of which goes through an interferometer and then into an infrared (IR) microscope. The light hits a sample and then that light is either reflected or transmitted through the sample onto a detector. As the moving mirror of the interferometer is shifted, the amplitude information on the detector is converted into spectral information though the use of a Fourier transform.

The issue with the existing approach is that the broadband, mid-IR source is a physically large source, so its diffraction limited spot is also very large. In order to look at small samples, rather than focusing the light down to those small spots, the light is apertured either before it hits the sample or before it hits the detector. The aperture blocks the light outside the field of interest. Therefore, the amount of energy hitting a small section of the sample of interest is a tiny fraction of the light initially entering the microscope. By the time the light hits the sample, it can be orders of magnitude less than the light that enters the microscope.

Furthermore, the light from the broadband mid-IR source has significant power (i.e., 250 milliWatts), but it is broadband, so if the person doing the measurements has only a few wavelength ranges of interest, there is no way to parse this out optically.

There are two problems with the FTIR microscope system. First, the user is dependent upon scanning the whole spectral range with an FTIR, to get the desired spectra of interest, which takes time. Second, the detector is often close to saturation from this mid-IR source, and further is saturated with wavelengths that are not of interest to the user. This diminishes the dynamic range of the detector in the wavelengths of highest interest.

The key practical problems with the existing approach include:

1. Measuring the spectral information on small sample sizes (i.e., 10 micrometer×10 micrometer spots or lower), often requires long measurement times to integrate enough light to obtain useful spectral information. This is a particular problem, with regard to time, when attempting to collect high spatial resolution measurements on a relatively large sample, where moving a stage from spot to spot is required to cover the entire sample.

2. Conversely, the user may choose severely degraded spectral information or spatial resolution (larger sample spots) to speed up the measurements.

3. It is difficult to obtain reflected spectral information on samples that are highly diffusive or absorbent.

4. It is difficult to obtain transmitted spectral information on samples that are relatively thick.

The advantage with a mid-IR semiconductor laser (QCL) based microscope is that more energy is delivered to a small spot of interest. This is because the laser is more powerful than the broadband, mid-IR source, but more importantly, the laser delivers a much smaller diffraction limited spot. So for many samples, there is no need to aperture the light. In cases where aperturing the light is required, the amount lost is much less than with the large than for a broadband Mid-IR source. This is especially true for a semiconductor laser in which the gain chip supports only a single spatial mode or only a few spatial modes, which translate to small beam sizes.

The present system combines a microscope with a widely tunable mid-IR laser. The advantage with this type of laser is that it is possible to obtain spectral information from the fingerprint region, which provides much more pronounced spectral peaks than in the NIR or visible. The widely tunable mid-IR absorption spectroscopy device described above provides the enabling technology that makes a mid-IR laser based microscopy system possible.

In one embodiment of the system, the tunable laser is pulsed at a wavelength, the light enters the microscope and then is either transmitted through a sample or reflected off of the sample onto a detector. The detector correlates the light that it collects with the wavelength of light that was transmitted by the laser. Then the laser pulses at the next wavelength in a range and the process repeats many times to build up a full spectrum of the material of interest. In a microscope where there is a scanning stage the electronics from the mid-IR laser system would be tied to the moving stage, so that the sample could be moved to the next point once the spectral information is collected.

The laser based system has the following advantages:

1. Light can focused onto small spots providing higher power on small samples, which translates into higher a signal to noise ratio (SNR). This means either higher quality spectral data or less time required to make a measurement.

2. There is more light on the sample, so that samples that do not return much light in conventional systems can be measured effectively using a laser based system.

3. The laser can be set to tune across a specific wavelength band of interest, speeding up measurements for applications, where looking at broadband spectra is not needed.

Additional configurations include a single detector, a linear detector, or a focal plane array. Also, it is possible to inject the laser beam into the FTIR rather than into the microscope directly.

Conventional FTIR microscope imaging systems are made from the ground up and do not use conventional microscopes as the basis for construction. This has been required to accommodate and optimize the interfacing with the FTIR instrument, to reduce ambient interferences, and to accommodate the mechanical parts required in the physical scanning of the sample on the microscope stage. In addition, they require the use of sophisticated optical systems incorporating expensive Cassegrain lenses, and there is the need for the use of liquid nitrogen cooled detectors, which are both large and expensive to purchase and maintain.

Figure 38:
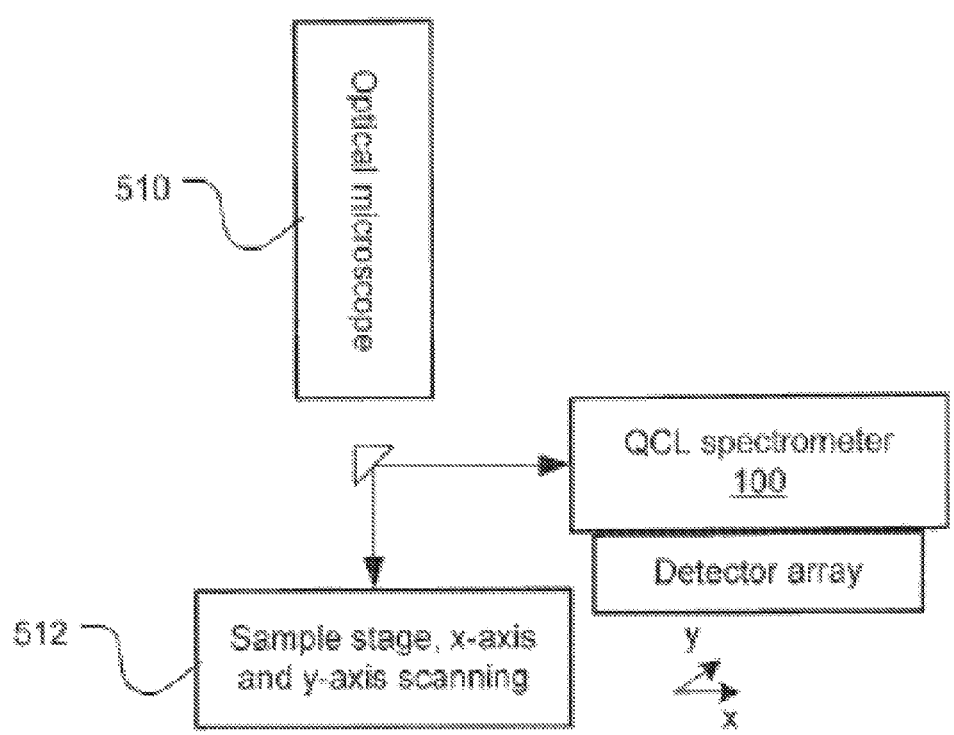
FIG. 38 is a block diagram of a QCL microscope.

FIG. 38 shows a QCL microscope system. It is much simpler and incorporates three basic elements: (1) a conventional light microscope 510, although Cassegrain objectives are used in some implementations for the 6-12 micron spectral range, (2) the QCL spectrometer 100 described above but with a detector array such as a MEMS-based microbolometer thermal detecting array, and (3) an x-y scanning stage 512 to scan the sample under the optical microscope 510 and the tunable signal from the QCL spectrometer. The spectral tuning range of a QCL spectrometer 100 is preferably 6.0 to 12 micrometers, which covers adequately the spectral region that is the most useful for medical diagnostics. Because of the relatively high power of the QCL, expensive, cooled detectors are not required. Furthermore the expensive optical systems associated with FTIR system are eliminated. Importantly, the QCL spectrometer is orders of magnitude faster than conventional FTIR imaging systems because the QCL system uses an extensive array to produce the image within minutes in contrast to conventional FTIR systems that scan the image much more slowly, often taking hours to produce a result.

Figure 39:
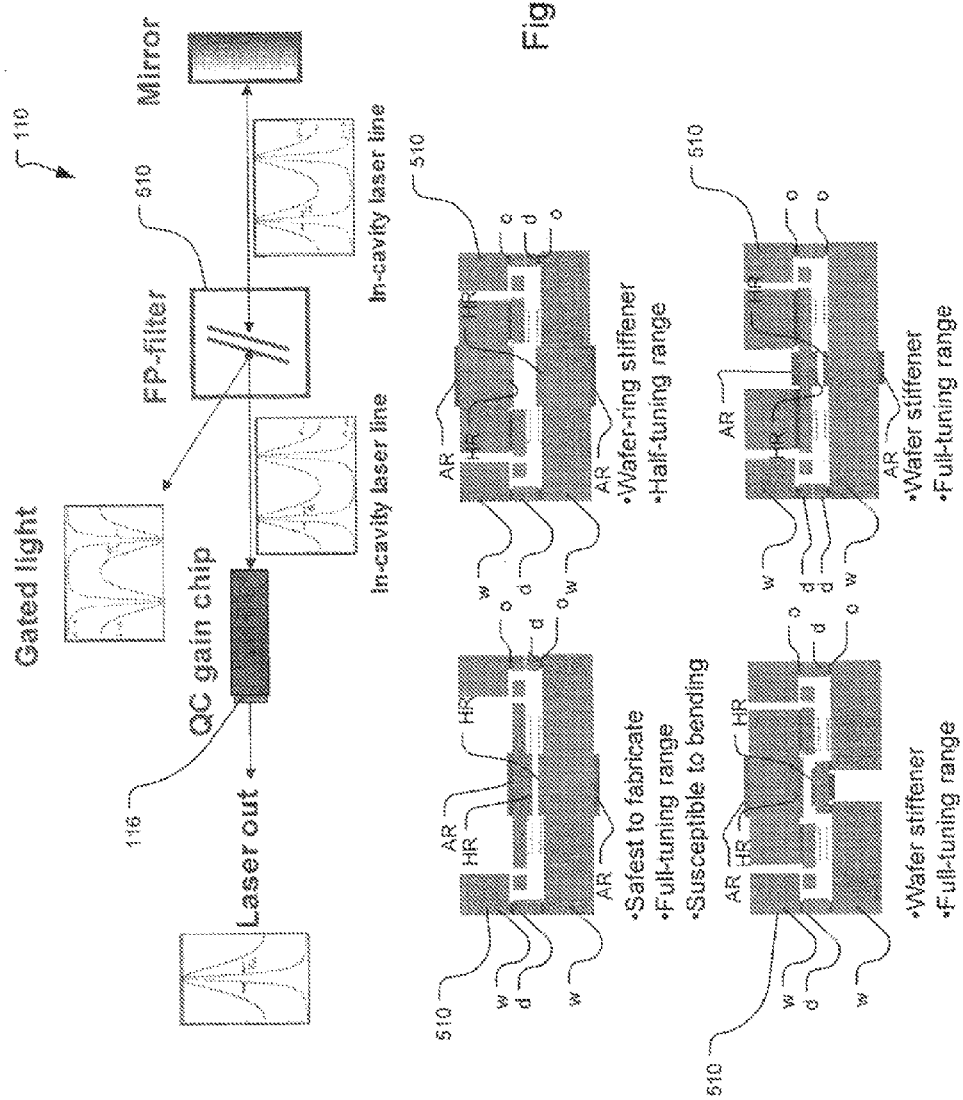
FIG. 39 shows an alternative QCL tunable laser configuration in which the grating tuner is replace with a Fabry-Perot tunable filter and four micro electrical mechanical system (MEMS) Fabry-Perot tunable filter configurations.

FIG. 39 shows an alternative QCL tunable laser 110 configuration in which the grating tuner is replace with a Fabry-Perot tunable filter 510 and a discrete back cavity mirror 512. This laser configuration replaced the grating tuned versions described previously in embodiments of the present invention;

Also shown are four micro electrical mechanical system (MEMS) Fabry-Perot tunable filter configurations. Generally, the device layer (d) thicknesses are about 10 micrometers, the buried oxide (o) thickness is 1 micrometer, and the wafer (w) thickness is 400 micrometers. Anti reflection coatings AR are used to improve coupling into the optical cavity defined by to highly reflecting layers HR.

Identification of Materials Using Automated Assessment of IR Spectral Data

Figure 40:
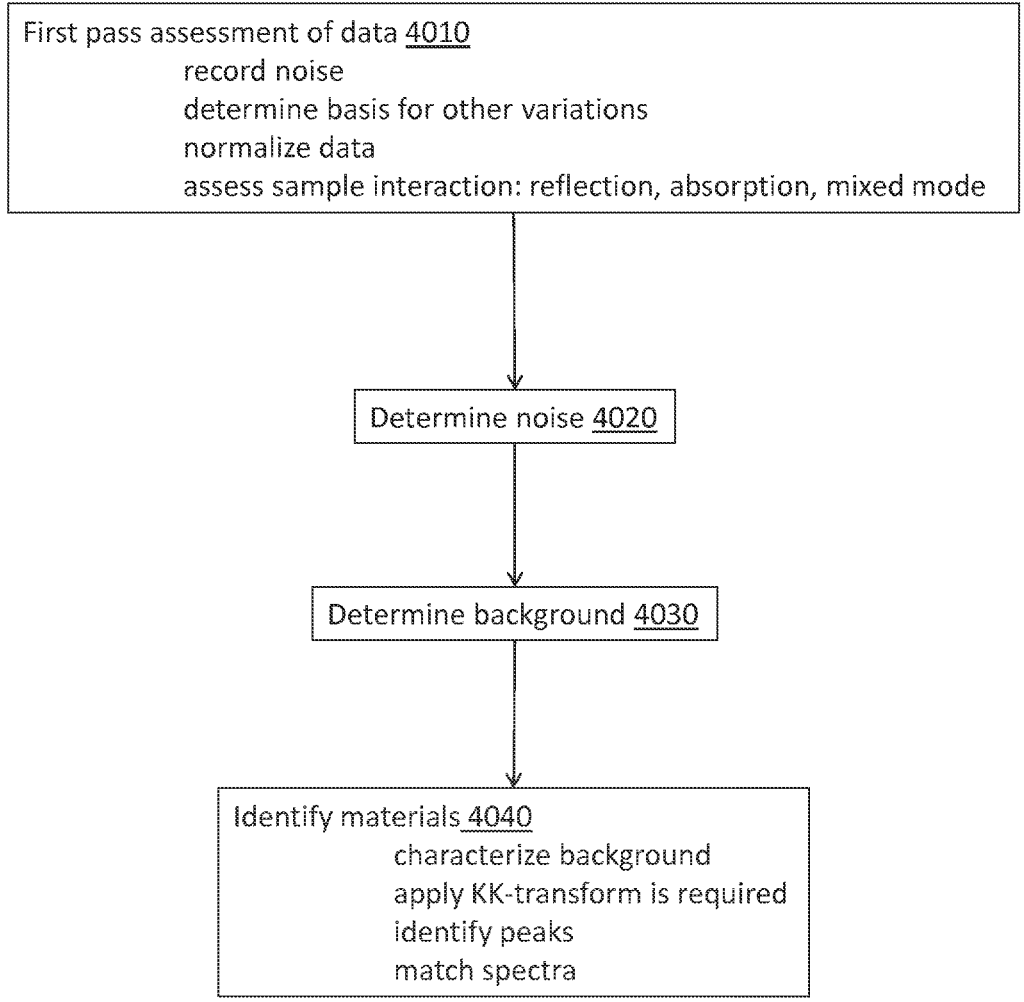
FIG. 40 is a flow diagram illustrating an automated method for identifying substances using the QCL spectroscopy system.

FIG. 40 shows a method for using the QCL spectroscopy system 100 in a identifying an unknown substance by automated assessment of spectral data.

In order to identify an unknown substance by infrared spectral measurements, it is necessary to step through a series of measurement scenarios and to narrow down the options that exist for the generation of the spectral signature. These are grouped into the following subsets: an initial or first-pass assessment of the data, the determination and characterization of noise sources, the characterization of the spectral background (what is a constant and what is a systematic variable), the differentiation of the analyte of interest (the unknown) from the background and how to determine if the unknown material is present in a mixture. These scenarios are often interrelated and one step in the process can be highly dependent on another.

.1. First-Pass Assessment

The first-pass assessment is made in step 4010. Here, the light level is very important for the first evaluation of the spectral signal as it can influence the way that the spectroscopy system 100 is used and the overall significance of the spectral signal. The light level can influence the efficiency of how the full digitization range of the detector system is used. The signal is digitized from zero light on the detector to full light on the detector, and this is governed by the detector response (and linearity) and the analog to digital converter used for the digitization. One assesses how much of the signal carried the useful information, its numerical significance, and how well the noise is represented. In order to characterize the noise correctly, in one of the important steps in the overall process, the noise is accurately recorded and represented.

Then, the basis for other variations in the signal are determined. Often these variations are influenced by the measurement system itself and the way that the light is captured. The sample itself can also be changing and those changes can range from the texture of the surface to changes in the material composition or morphology at the sample surface as viewed (for solids and liquids). When a spectrometer is viewing a changing field of information, the light level is a fundamental element as indicated above, and in order to capture the signal and its nuances the resolution and linearity of the measurement system become important factors. In the final steps the data are normalized for comparison purposes and it is important that the raw data were captured as accurately as possible.

The spectral content of a sample is influenced by the method used to collect spectral data, including the physics of the light interaction at the surface of the sample and the absorption characteristics of the sample and its substrate. It depends on whether only the surface of the sample/substrate interacts or the bulk of the material interacts. When the interaction is purely on the surface the refractive index of the material becomes a dominant factor, whereas if penetration into the bulk occurs then the spectral content is governed by absorption. In many circumstances it is not clear cut, and both mechanisms occur giving rise to a mixed mode of interaction. The result is a complex signal that is characteristic of the material but does not conform to an immediately recognizable signature.

As described above, there are many methods used for the sampling of materials by QCL spectroscopy. The method required for the measurement (contact or non-contact) tends to dictate the method selected. Solids and liquids may be sampled by methods that involve sample contact, such as with the ATR probe, or otherwise, such as stand-off. In the former case an absorption-like signature is obtained. In cases of stand-off measurement the mixed mode scenario discussed above is determined by whether the measurement involves a specular (mirror-like) or diffuse measurement from the sample. For gases, the mode of measurement is in most cases absorption based, whether the gas is contained in a gas cell or is free in an open path scenario. The main exception is where an emission mode of measurement is made.

In the end, the spectrum of a sample is recognized and identified by the presence of characteristic signatures. Ideally these are well defined signatures that contain peaks related to the specific chemical species that are to be detected. In mixed mode scenarios the appearance of the peaks may be distorted, but if the signature is representative of the material under investigation then even distorted data should be able to be correlated back to that material(s) of interest. For automated processing of the data, the presence and nature of "peaks' within the spectral data are determined. Algorithms are capable of handling non-standard spectral signatures and waveforms.

2. Determination of Noise

In step 4020, the noise is determined. In a practical system. noise is defined as information that is varying on a random or systematic basis that is not directly linked to the signal of interest (the spectral signal). Both signals can be varying, and it is important to differentiate and separate both signals. Note that noise can be present in the signature that originates from a background or interference. It is important to isolate this component in order to obtain the spectral information of the target of interest. Spectral noise from the background is treated the same as the sample spectrum in collection and is treated differently at the end of the identification process.

Electronic Noise—random/systematic—Random noise is usually the easiest noise source to handle if it is truly random. If there are also systematic noise sources in a system they are identified and selectively removed. Such signatures are identified and corrected prior to the spectral measurement.

Sample Noise—mixture of random and systematic—This is more difficult to identify and handle. An example covered above is where there is more than one mode of measurement of where the signal level from the sample is fluctuating. This is handled in the data collection process by the use of autocorrelation methods, and in spectral matching to known and expected signatures. Signals that are correlated are separated from the non-correlated signatures.

Spectral Interference—systematic—in this situation the signal is first treated as spectral data. One then monitors the signal to see if it is changing. Spectral interferences are treated as backgrounds. If a signal is changing then it is important to determine how it is changing and is it is systematic or random. Systematic signals are extracted by cross correlation methods and these are combined with spectral differentiation procedures to separate the background from the sample signature. The spectral signatures from interferences that can be identified are used later to both differentiate and quantitate the relative amounts of sample versus background in the overall signature.

3. Background Assessment

In step 4030, a determination of the background is made. Preferably this determination of background is made by correlation methods. This is linked to the assessment discussed above. In a dynamic measurement situation the current spectral signature is compared to the most previous signature, and other previous signatures. The signature of the background is assumed to be the most constant and is used for separating background from the signature a different material. In a static measurement situation the background is normally determined and recorded separately prior to the actual measurement.

Detection of background changes—In a dynamic measurement when a background has been identified as a background, it is compared to the most current signatures by correlation and closeness of fit methods. Differences observed are then linked to the presence of another substance or chemical species. The background signatures are highly correlated, and a loss of correlation signifies the presence of another material.

Detection of contamination—in a dynamic situation, a change in background is detected from the spectral signatures, which are first correlated to the established background. A loss of correlation indicates the presence of contamination. The spectral contamination is the differentiated from the background by the use of spectral fitting (such as least squares fitting) or spectral subtraction methods. Once the spectral signature of the contaminant is extracted it is further characterized by comparison to known signatures of target compounds.

4. Identification of Materials

The material are then identified in step 4040. This process includes a series of substeps.

Characterization of the background—the background of a spectrum is either pre-determined or determined in real-time as discussed above. In some cases it is important to characterize the background because if identified, it is used later to differentiate it from a contaminant spectrum that is measured in the presence of that background. If the material (solid, liquid or gas) has a characteristic signature then it can be matched to a stored library of compounds and substances.

Determination of the spectrum type—absorption vs. refractive index—the importance of spectrum type was mentioned earlier. If the spectrum is mixed mode then it will be distorted. If the type of distortion is known, then algorithms, such as the KK-transform, are applied to convert the spectral data into a more consistent and recognizable format.

Peak-based identification—digital mask—this assumes that identifiable peaks can be discerned. If they can and the peak positions can be determined, then a quick sort and identification will be performed by the use of a simple binary mask. In this case the presence or absence of a peak is determined by simple Boolean algebra. This can be assessed as an absolute match (presence and absence weighted) or a positive match (just based on presence). The identification is then made based on a set of binary codes stored for known substances.

Peak-based identification—peak table—this is a more discriminating method of identification than the simple binary approach, where peak height (or relative peak height) is taken into account. Also, peak table based algorithms can be designed to accommodate peaks shifts caused by chemical interactions or physical interactions, and other parameters, such as width may be used as a differentiating factor. Often an exact match to both peak position and height is sufficient for an absolute match, as long as there are a statistically significant number of peaks present. Fuzzy logic is applied peak matching methods in some examples to accommodate spectral shifts and variances caused by physical, environmental or chemical interaction effects.

Spectral matching based on correlation—a wide range of correlation methods exist, and these range from cross-product type correlations to goodness of fit methods. Dependent of the nature of the spectrum (broad features vs. narrow, well defined features) the goodness of fit methods are often more differentiating and are better for separating minor differences in spectral data. Note that for absolute identifications, correlation methods that can be weighted by the presence and location of peaks are often required.

5. Handling Mixtures

Treating mixtures as single entities—mixtures can be stored in a library and compared directly to the unknown. The unknown is then identified as that mixture or a close fit to that mixture. For example, a formulated product is most likely to be a mixture on chemical substances, with one or two being dominant. In terms of identification it is often more practical to identify the material as that "product" rather than attempt to identify the components, unless the intent is to identify and measure the amounts of the major components. If the material is to be measured as a single entity then its ID can be based on its overall spectrum using methods described above. If quantification is required, then simple "absorbance" based Beer's Law measurements or simple least squares fitting can be applied.

Simple resolution of mixtures—Determining what is present in a mixture can be performed by using a simple peak-based or binary match where positive, rather than absolute presence of peaks/features is used in the library match. If a major component is identified, then one approach is to subtract out the major component spectrum and then re-apply the spectral search to the spectral residue (following subtraction). Using this approach other components of mixtures can be identified and this can be performed at least twice from good quality spectral data. Beyond two or three applications of the subtraction method the residual data becomes too distorted by artifacts and noise to be useful in further subtractions. In terms of quantitative measurement, if scaling is required in the spectral subtraction procedure, then the amount of scaling applied can be used to provide a quantitative estimate of the relative amount present of that particular component. If the components are sufficiently well identified, then simple Beer's Law methods are applied, and a matrix based solution may be used in cases of significant spectral overlap of the individual components.

Multivariate modeling of mixtures—If a mixture is not well characterized then methods based on multivariate modeling are preferably used. These are often difficult to manage and usually require multiple reference spectra that represent the variances of composition within the material of interest. This requires a good data base of reference substances. Factor analysis may be used as a method to look for similarities in materials and to extract spectra of common spectral significance. Methods considered can range from simple MLR (multiple linear regression) to neural network approaches.

While this invention has been particularly shown and described with references to preferred embodiments thereof, it will be understood by those skilled in the art that various changes in form and details may be made therein without departing from the scope of the invention.

What is claimed is:

1. A spectroscopy system comprising:
   at least two laser modules, each of the laser modules including a laser cavity, a quantum cascade gain chip for amplifying light within the laser cavity, and a tuning element for controlling a wavelength of light generated by the modules;
   combining optics for combining the light generated by the at least two laser modules into a single beam;
   a reference detector for measuring the wavelength of the single beam; and
   a sample detector for detecting an absorption spectra of a sample from the single beam returning from the sample, the system comparing the absorption spectra with a standard to analyze the sample based upon the comparison.

2. The spectroscopy system of claim 1, further comprising three of the laser modules.

3. The spectroscopy system of claim 1, wherein the tuning element comprises a grating.

4. The spectroscopy system of claim 1, wherein the tuning element comprises a Fabry-Perot tunable filter.

5. The spectroscopy system of claim 1, further comprising projection optics for projecting the single beam to a sample.

6. The spectroscopy system of claim 1, further comprising a sighting laser and a housing with attached handle, wherein the laser modules are contained within the housing.

7. The spectroscopy system of claim 6, wherein the system operates on 30 Watts or less.

8. The spectroscopy system of claim 6, further comprising a soil marking device.

9. The spectroscopy system of claim 1, wherein the sample detector is separated from the laser modules.

10. The spectroscopy system of claim 1, further comprising retroreflectors positioned in a room, wherein the single beam is projected to the retroreflectors and then returned to the sample detector.

11. The spectroscopy system of claim 1, further comprising a gas cell and a portable hand-held housing, wherein the laser modules and the gas cell are contained within the housing, the single beam analyzing air in the gas cell.

12. The spectroscopy system of claim 1, further comprising a system for puffing air onto shoes and a system for collecting the air, the single beam analyzing the collected air.

13. The spectroscopy system of claim 12, further comprising a magnetometer.

14. The spectroscopy system of claim 1, further comprising a portable housing, a fiber optic probe and a fiber optic cable, wherein the fiber optic cable connects the spectroscopy system to the fiber optic probe.

15. The spectroscopy system of claim 14, wherein the fiber optic probe is a grazing angle probe.

16. The spectroscopy system of claim 14, wherein the fiber optic probe is an attenuated total reflection probe.

17. The spectroscopy system of claim 16, wherein the attenuated total reflection probe is triangular prism, trapezoidal prism, or geometric principle.

18. The spectroscopy system of claim 16, wherein the fiber optic cable is a silver halide cable.

19. A quantum cascade laser microscopy system comprising:
   the spectroscopy system claimed in claim 1,
   a light microscope for projecting the single beam onto the sample, and
   an X-Y scanning stage for scanning the sample under the microscope.

20. The quantum cascade laser microscopy system of claim 19, wherein the detector is a linear detector or a focal plane array.

21. The quantum cascade laser microscopy system of claim 19, wherein a spectral tuning range includes 6 to 12 micrometers.

\* \* \* \* \*